(12) United States Patent
Hursan et al.

(10) Patent No.: US 10,190,999 B2
(45) Date of Patent: Jan. 29, 2019

(54) NUCLEAR MAGNETIC RESONANCE AND SATURATION WELL LOGS FOR DETERMINING FREE WATER LEVEL AND RESERVOIR TYPE

(71) Applicant: Saudi Arabian Oil Company, Dhahran (SA)

(72) Inventors: Gabor Hursan, Dhahran (SA); Shouxiang Ma, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 351 days.

(21) Appl. No.: 15/151,896

(22) Filed: May 11, 2016

(65) Prior Publication Data

US 2017/0328847 A1    Nov. 16, 2017

(51) Int. Cl.
*G01V 3/00* (2006.01)
*E21B 43/16* (2006.01)
*G01N 24/08* (2006.01)
*G01V 3/32* (2006.01)

(52) U.S. Cl.
CPC ............. *G01N 24/081* (2013.01); *G01V 3/32* (2013.01); *Y02A 90/344* (2018.01)

(58) Field of Classification Search
CPC ........ G01N 24/08; G01N 24/081; G01V 3/32; G01V 3/38; G01V 3/14; G01V 3/44;
(Continued)

(56) References Cited

U.S. PATENT DOCUMENTS 4,885,540 A * 12/1989 Snoddy .................. G01R 33/44
324/303

6,008,645 A    12/1999 Bowers et al.
6,833,699 B2   12/2004 Galford et al.
7,755,354 B2   7/2010 Akkurt
(Continued)

FOREIGN PATENT DOCUMENTS

WO    2014137863 A2    9/2014

OTHER PUBLICATIONS

International Search Report and Written Opinion for International Application No. PCT/US2017/032059; dated Jul. 6, 2017 (pp. 1-13).

(Continued)

*Primary Examiner* — Minh N Tang
(74) *Attorney, Agent, or Firm* — Bracewell LLP; Constance G. Rhebergen; Christopher L. Drymalla

(57) ABSTRACT

Provided in some embodiments are systems and methods for determining characteristics of a hydrocarbon reservoir. Embodiments include conducting a nuclear magnetic resonance (NMR) logging operation of a targeted reservoir section of a wellbore extending into a hydrocarbon reservoir to generate a NMR log of the targeted reservoir section, conducting a resistivity logging of the targeted reservoir section to generate an uninvaded water saturation ($S_w$) log of the targeted reservoir section, determining for each of a plurality of depths in the section, a $T_2$ cutoff point based on values of the NMR and $S_w$ logs, identifying a subset of the $T_2$ cutoff points that exhibit a hyperbolic trend, determining a theoretical cutoff curve corresponding to the subset of the $T_2$ cutoff points, determining a free water level (FWL) of the reservoir based on the theoretical cutoff curve, and determining a rock type of the reservoir based on the theoretical cutoff curve.

25 Claims, 11 Drawing Sheets

(58) Field of Classification Search
CPC ........ E21B 43/24; E21B 43/30; E21B 43/243; E21B 43/247
See application file for complete search history.

(56) References Cited

U.S. PATENT DOCUMENTS

| | | | |
|---|---|---|---|
| 8,217,337 | B2 | 7/2012 | Neville et al. |
| 8,452,538 | B2 | 5/2013 | Klein et al. |
| 8,736,263 | B2 | 5/2014 | Minh |
| 2003/0094946 | A1* | 5/2003 | Galford ............... G01V 3/32 324/303 |
| 2009/0198446 | A1 | 8/2009 | Hursan |
| 2009/0248309 | A1 | 10/2009 | Neville et al. |
| 2013/0103319 | A1 | 4/2013 | Buiting et al. |
| 2013/0131989 | A1 | 5/2013 | Buiting et al. |
| 2014/0257702 | A1 | 9/2014 | Al-Ibrahim et al. |
| 2015/0198036 | A1 | 7/2015 | Kleinberg et al. |

OTHER PUBLICATIONS

Jocobsen, et al.: "Improved Reservoir Evaluation in Norway Wells From High-Resolution Producibility Measurements" Proceedings of the European Petroleum; vol. 2, Oct. 20, 1998; pp. 81-91.

Morris et al.: "Using Log-Derived Values of Water Saturation and Porositz" SPWLA 8th Annual Logging Symposium, Jun. 12, 1967; pp. 1-26.

Glorioso, Juan Carlos, et al. "Deriving Capillary Pressure and Water Saturation from NMR Transversal Relaxation Times" SPE 81057, SPE Latin American and Caribbean Petroleum Engineering Conference, Trinidad, West Indies, Apr. 27-30, 2003; pp. 1-13.

Altunbay, M., et al. "Capillary Pressure Data from NMR Logs and Its Implications on Field Economics" SPE 71703, SPE Annual Technical Conference and Exhibition, New Orleans, Louisiana, Sep. 30-Oct. 1, 2001; pp. 1-10.

Volokitin, Yakov, et al. "A Practical Approach to Obtain Primary Drainage Capillary Pressure Curves from NMR Core and Log Data" Petrophysics, vol. 42, No. 4 (Jul.-Aug. 2001); pp. 334-343.

"V. General Reservoir Characteristics" available at https://www.princeton.eduk~ota/disk3/1977/7710/771007.PDF, accessed on Feb. 18, 2016.

"Nuclear magnetic resonance (NMR) logging" available at http://petrowiki.org/Nuclear_magnetic_resonance_(NMR)_logging, accessed on Feb. 18, 2016.

\* cited by examiner

NUCLEAR MAGNETIC RESONANCE AND SATURATION WELL LOGS FOR DETERMINING FREE WATER LEVEL AND RESERVOIR TYPE

FIELD OF INVENTION

The present invention relates generally to determining characteristics of hydrocarbon reservoirs, and more particularly to using nuclear magnetic resonance (NMR) and water saturation well logs to determine reservoir free water level (FWL) and rock type.

BACKGROUND OF THE INVENTION

A petroleum (or oil and gas) reservoir is a subsurface pool of hydrocarbons trapped in subsurface porous rock formations. Oil and gas wells are often drilled into these subsurface reservoirs to extract the trapped hydrocarbons. It can be beneficial to understand the characteristics of rocks penetrated by the well, including the characteristics of the formation surrounding the well, as knowledge of the characteristics can help with critical decisions that need to be made during completion and production of the well. For example, reservoir characteristics can be used to determine whether the formation contains hydrocarbons, to estimate the amount of hydrocarbons in the formation, to predict the ability to extract (or produce) the hydrocarbons, and to determine optimal techniques for drilling the well and producing the hydrocarbons from the well.

Reservoir characteristics of interest can include formation porosity, formation permeability, resistivity, water saturation, free water level (FWL), and the like. Porosity indicates how much space exists in a particular formation, where oil, gas, and/or water may be trapped. Permeability indicates the ability of liquids and gases to flow through the formation. Resistivity indicates how strongly the formation (rock and fluids) opposes the flow of electrical current, and can be indicative of the porosity of the formation and the presence of hydrocarbons. For example, resistivity may be relatively low for a formation that has high porosity and a large amount of water, and resistivity may be relatively high for a formation that has low porosity or contains a large amount of hydrocarbons. Water saturation indicates the fraction of water in a given pore space. FWL is a level (or depth) below the lower boundary of the hydrocarbons in the reservoir, and at which the capillary pressure between water and oil is zero. Above the FWL, the reservoir is expected to produce hydrocarbons or water depending on oil and water relative permeability; below the FWL, the reservoir can produce only water. Reservoir characteristics can be determined using a variety of different techniques. For example, certain characteristics can be determined via coring (e.g., physical extraction of rock samples) or logging operations (e.g., wireline logging, logging-while-drilling (LWD) and measurement-while-drilling). Coring operations include physically extracting a rock sample from the target reservoir through a wellbore for detailed laboratory analysis. For example, when drilling an oil or gas well a coring bit can cut plugs (or "cores") from the formation and bring them to the surface, and these samples can be analyzed at the surface (e.g., in a lab) to determine various characteristics of the formation at the location where the sample was taken from. Although a coring approach can be very effective in determining reservoir characteristics, it can be time consuming and expensive. Logging operations typically include lowering one or more measurement tools into a wellbore, and recording measurements as the tool traverses the wellbore. The plot of the measurements versus depth is referred to as a "log". Logs can be analyzed to determine some characteristics of the well (e.g., including characteristics of the reservoir penetrated by the well), while other characteristics may be difficult to determine using only logs.

There are many different types of logging available, and a particular form of logging may be selected and used based on the logging conditions and the type of measurements to be acquired. For example, nuclear magnetic resonance (NMR) logging measures the induced magnetic moment of hydrogen nuclei (protons) contained within the fluid-filled pore space of porous media (reservoir rocks). Unlike some conventional logging measurements (e.g., acoustic, density, neutron, and resistivity), which respond to both the rock matrix and fluid properties and are strongly dependent on mineralogy, NMR logging measurements respond to the presence of hydrogen protons only. Because these protons primarily occur in pore fluids, NMR effectively responds to the volume, composition, viscosity, and distribution of these fluids (e.g., oil, gas, water). NMR logs provide information about the quantities of fluids present, the properties of these fluids, and the sizes of the pores containing these fluids, and using this information, it may be possible to infer or estimate the volume (porosity) and distribution (permeability) of the rock pore space, and the like. With regard to measurement of the nuclear magnetic properties of formation hydrogen, the basic core and log measurement is the $T_2$ decay, presented as a distribution of $T_2$ amplitudes versus decay time at each sample depth, typically from about 0.3 ms (milliseconds) to about 3 s (seconds). The $T_2$ decay is processed to give the total pore volume (the total porosity) and pore volumes within different ranges of $T_2$. As a further example of logging techniques, resistivity logging measures the electrical resistivity of rock or sediment in and around a borehole. Resistivity measurements obtained via such logging can be used to determine corresponding reservoir water saturation ($S_w$). Accordingly, resistivity logging can be used to generate corresponding water saturation ($S_w$) logs along a wellbore.

SUMMARY OF THE INVENTION

Applicants have recognized that, although some current logging and log analysis techniques can be useful for determining some well characteristics (e.g., including characteristics of the reservoir penetrated by the well), certain well characteristics cannot be accurately determined using current logging and log analysis techniques. For example, although well (and reservoir) characteristics such as porosity, permeability, the presence of hydrocarbons, and resistivity, can be estimated using certain logging and log analysis techniques, these logging and analysis techniques may not provide an accurate determination for other well characteristics, such as free-water-level (FWL) and rock type. In view of this, well operators often have to employ time consuming and costly techniques, such as coring, to obtain estimates for these and other well characteristics. For example, to determine FWL using present techniques a rigorous core-based petrophysical reservoir typing (PRT) calibration may need to be conducted.

Recognizing these and other shortcomings of existing systems, Applicants have developed novel systems and associated methods for generating nuclear magnetic resonance (NMR) well logs and water saturation ($S_w$) well logs for a well, and using the NMR and water saturation ($S_w$) well logs to determine reservoir free water level (FWL) and/or rock type for the well. In some embodiments, a well is drilled (e.g., according to a predefined protocol) and logging is conducted to obtain NMR and water saturation ($S_w$) logs for the well. The logs may then be processed to determine the free water level (FWL) and/or rock type for the well. For example, water saturation $T_2$ cutoff points are determined across a depth interval of interest (e.g., a targeted reservoir section) using the NMR and water saturation ($S_w$) logs, a subset of the water saturation $T_2$ cutoffs points that exhibit hyperbolic trend are selected, a theoretical water saturation ($S_w$) cutoff curve is generated using the subset of the water saturation ($S_w$) $T_2$ cutoff points (e.g., via curve fitting to the subset of points using two fitting parameters: a scaling factor (a) and a height above the FWL (HAFWL)), and the free water level (FWL) and/or rock type for the well is determined using the theoretical water saturation ($S_w$) cutoff curve (e.g., using the determined scaling factor (a) and a $T_2$ value on the curve corresponding to a given depth and HAFWL). Accordingly, the free water level (FWL) and/or rock type for the well can be determined using NMR and water saturation ($S_w$) logs for the well, without the use of a core-based PRT calibration. That is, the free water level (FWL) and/or rock type for the well may be determined without engaging in coring processes that can be time consuming and expensive.

In some embodiments, provided is a method for determining free water level (FWL) and rock type of a hydrocarbon reservoir. The method including drilling a well including a wellbore extending into a formation of a hydrocarbon reservoir, the wellbore including a targeted reservoir section, and drilling the well including drilling the targeted reservoir section with steady overbalanced pressure to facilitate mud filtrate flushing, conducting a nuclear magnetic resonance (NMR) logging operation of the targeted reservoir section to generate a nuclear magnetic resonance (NMR) log of the targeted reservoir section, conducting a resistivity logging of the targeted reservoir section to generate an uninvaded water saturation ($S_w$) log of the targeted reservoir section, determining, for each of a plurality of depths within the targeted reservoir section, a $T_2$ cutoff point for the depth that corresponds to a decay time at which a buoyancy pressure of hydrocarbon is about equal to reservoir capillary pressure (controlled by pore throats, interfacial tension between the immiscible pore fluids, and interaction between fluids and rock surfaces) at the depth, the $T_2$ cutoff for the depth determined based on a $T_2$ distribution of the NMR log for the depth, and a saturation ($S_w$) value of the uninvaded water saturation ($S_w$) log for the depth, identifying a subset of the $T_2$ cutoff points across a subset depth interval in the targeted reservoir section that exhibit a hyperbolic trend, conducting a curve fitting operation to determining a theoretical cutoff curve for the subset of the $T_2$ cutoff points, the curve fitting operation including a fitting based on a scaling factor (a) parameter and a depth parameter corresponding to a height above free water level (HAFWL), determining a FWL of the reservoir based on, for at least one point on the theoretical cutoff curve, a true vertical depth for the point and an HAFWL for the point on the theoretical cutoff curve, and determining a rock type of the reservoir corresponding to the scaling factor (a).

In certain embodiments, drilling the well includes adding surfactant to a water based mud (WBM) used in the drilling process to facilitate reduced interfacial tension to maximize sweep in a flushed zone of the wellbore. In certain embodiments, conducting the NMR logging operation of the targeted reservoir section to generate the NMR log of the targeted reservoir section includes minimizing an echo spacing (TE) of the NMR logging operation, and employing a relatively large number of echoes. In certain embodiments, conducting the resistivity logging of the targeted reservoir section to generate the uninvaded water saturation ($S_w$) log of the targeted reservoir section includes acquiring triple combo logs and performing uninvaded reservoir water saturation analysis of the triple combo logs.

In some embodiments, provided is a method for determining characteristics of a hydrocarbon reservoir. The method including: conducting a nuclear magnetic resonance (NMR) logging operation of a targeted reservoir section of a wellbore extending into a hydrocarbon reservoir to generate a nuclear magnetic resonance (NMR) log of the targeted reservoir section, conducting a resistivity logging of the targeted reservoir section to generate an uninvaded water saturation ($S_w$) log of the targeted reservoir section, determining, for each of a plurality of depths in the targeted reservoir section, a $T_2$ cutoff point for the depth based on values of the NMR log and the uninvaded water saturation ($S_w$) log for the depth, identifying a subset of the $T_2$ cutoff points that exhibit a hyperbolic trend, determining a theoretical cutoff curve corresponding to the subset of the $T_2$ cutoff points, determining a FWL of the reservoir based on the theoretical cutoff curve, and determining a rock type of the reservoir based on the theoretical cutoff curve.

In certain embodiments, the method includes drilling the well, and the drilling of the well includes drilling the targeted reservoir section with steady overbalanced pressure to facilitate reduced interfacial tension to maximize sweep in a flushed zone of the wellbore. In certain embodiments, the drilling of the well includes adding surfactant to a water based mud (WBM) used in the drilling process to facilitate reduced interfacial tension to maximize sweep in a flushed zone of the wellbore.

In certain embodiments, conducting the NMR logging operation of the targeted reservoir section to generate the NMR log of the targeted reservoir section includes minimizing the TE of an NMR data set. In certain embodiments, conducting the NMR logging operation of the targeted reservoir section to generate the NMR log of the targeted reservoir section includes employing a relatively large number of echoes. In certain embodiments, conducting the resistivity logging of the targeted reservoir section to generate the uninvaded water saturation ($S_w$) log of the targeted reservoir section includes acquiring triple combo logs and performing uninvaded reservoir water saturation analysis of the triple combo logs.

In certain embodiments, the $T_2$ cutoff point for each depth corresponds to a time at which a buoyancy pressure of hydrocarbon is about equal to pore capillary pressure at the depth, the $T_2$ cutoff determined based on a $T_2$ distribution of the NMR log for the depth, and a saturation ($S_w$) value of the uninvaded water saturation ($S_w$) log for the depth. In certain embodiments, determining a theoretical cutoff curve corresponding to the subset of the $T_2$ cutoff points includes using a curve fitting operation considering a fit to the subset of the $T_2$ cutoff points based on a scaling factor (a) parameter and a depth parameter corresponding to a height above free water level (HAFWL). In certain embodiments, determining a FWL of the reservoir based on the theoretical cutoff curve includes determining, for at least one point on the theoretical cutoff curve, a true vertical depth for the point and an HAFWL for the point on the theoretical cutoff curve, and wherein the FWL is a summation of the true vertical depth for the point and the HAFWL for the point. In certain embodiments, determining a rock type of the reservoir based on the theoretical cutoff curve includes determining a rock type of the reservoir corresponding to the scaling factor (a).

In some embodiments, provided is a system for determining characteristics of a hydrocarbon reservoir. The system including a logging system and a control unit. The logging system including a nuclear magnetic resonance (NMR) logging system adapted conduct a nuclear magnetic resonance (NMR) logging operation of a targeted reservoir section of a wellbore extending into a hydrocarbon reservoir to generate a nuclear magnetic resonance (NMR) log of the targeted reservoir section, and a resistivity logging system adapted to conduct a resistivity logging of the targeted reservoir section to generate an uninvaded water saturation ($S_w$) log of the targeted reservoir section. The control unit adapted to determine, for each of a plurality of depths in the targeted reservoir section, a $T_2$ cutoff point for the depth based on values of the NMR log and the uninvaded water saturation ($S_w$) log for the depth, identify a subset of the $T_2$ cutoff points that exhibit a hyperbolic trend, determine a theoretical cutoff curve corresponding to the subset of the $T_2$ cutoff points, determine a FWL of the reservoir based on the theoretical cutoff curve, and determine a rock type of the reservoir based on the theoretical cutoff curve.

In certain embodiments, the system includes a drilling system adapted to drill the well, and the drilling of the well includes drilling the targeted reservoir section with steady overbalanced pressure to facilitate reduced interfacial tension to maximize sweep in a flushed zone of the wellbore. In certain embodiments, the drilling of the well includes adding surfactant to a water based mud (WBM) used in the drilling process to facilitate reduced interfacial tension to maximize sweep in a flushed zone of the wellbore.

In certain embodiments, conducting the NMR logging operation of the targeted reservoir section to generate the NMR log of the targeted reservoir section includes minimizing the TE of the NMR logging operation. In certain embodiments, conducting the NMR logging operation of the targeted reservoir section to generate the NMR log of the targeted reservoir section includes employing a relatively large number of echoes. In certain embodiments, conducting the resistivity logging of the targeted reservoir section to generate the uninvaded water saturation ($S_w$) log of the targeted reservoir section includes acquiring triple combo logs and performing uninvaded reservoir water saturation analysis of the triple combo logs.

In certain embodiments, the $T_2$ cutoff point for each depth corresponds to a decay time at which a buoyancy pressure of hydrocarbon is about equal to pore capillary pressure at the depth, the $T_2$ cutoff determined based on a $T_2$ distribution of the NMR log for the depth, and a saturation ($S_w$) value of the uninvaded water saturation ($S_w$) log for the depth. In certain embodiments, determining a theoretical cutoff curve corresponding to the subset of the $T_2$ cutoff points includes using a curve fitting operation considering a fit to the subset of the $T_2$ cutoff points based on a scaling factor (a) parameter and a depth parameter corresponding to a height above free water level (HAFWL). In certain embodiments, determining a FWL of the reservoir based on the theoretical cutoff curve includes determining, for at least one point on the theoretical cutoff curve, a true vertical depth for the point and an HAFWL for the point on the theoretical cutoff curve, and wherein the FWL is a summation of the true vertical depth for the point and the HAFWL for the point. In certain embodiments, determining a rock type of the reservoir based on the theoretical cutoff curve includes determining a rock type of the reservoir corresponding to the scaling factor (a).

In some embodiments, provided is a non-transitory computer readable medium including program instructions stored thereon for determining characteristics of a hydrocarbon reservoir, the program instructions executable by one or more computer processors to perform the following: conducting a nuclear magnetic resonance (NMR) logging operation of a targeted reservoir section of a wellbore extending into a hydrocarbon reservoir to generate a nuclear magnetic resonance (NMR) log of the targeted reservoir section, conducting a resistivity logging of the targeted reservoir section to generate an uninvaded water saturation ($S_w$) log of the targeted reservoir section, determining, for each of a plurality of depths in the targeted reservoir section, a $T_2$ cutoff point for the depth based on values of the NMR log and the uninvaded water saturation ($S_w$) log for the depth, identifying a subset of the $T_2$ cutoff points that exhibit a hyperbolic trend, determining a theoretical cutoff curve corresponding to the subset of the T2 cutoff points, determining a FWL of the reservoir based on the theoretical cutoff curve, and determining a rock type of the reservoir based on the theoretical cutoff curve.

Figure 1A:
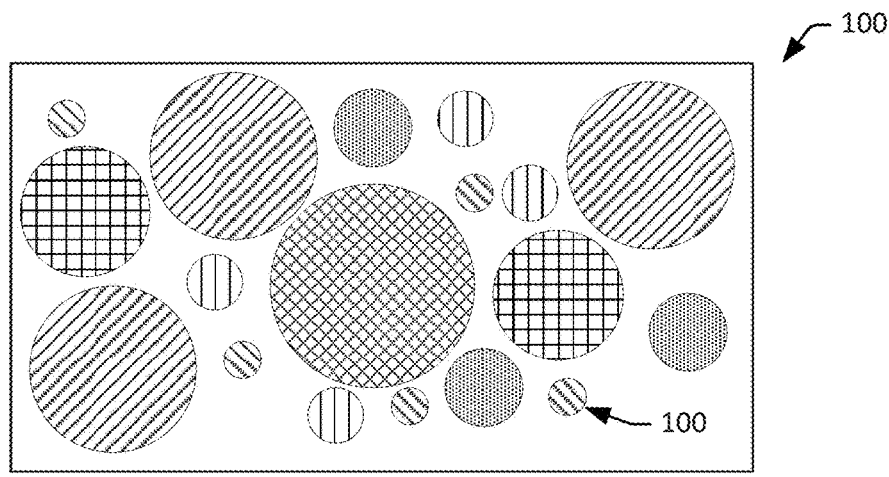
FIG. 1A is diagram that illustrates a representation of a grouping of multiple pores of a formation in accordance with one or more embodiments.

While this disclosure is susceptible to various modifications and alternative forms, specific embodiments thereof are shown by way of example in the drawings and will be described in detail herein. The drawings may not be to scale. It should be understood, however, that the drawings and the detailed descriptions thereto are not intended to limit the disclosure to the particular form disclosed, but, to the contrary, the intention is to cover all modifications, equivalents, and alternatives falling within the spirit and scope of the present disclosure as defined by the appended claims.

DETAILED DESCRIPTION

The present invention will now be described more fully hereinafter with reference to the accompanying drawings in which example embodiments of the invention are shown. This invention may, however, be embodied in many different forms and should not be construed as limited to the illustrated embodiments set forth herein, rather, these example embodiments are provided so that this disclosure will be thorough and complete, and will fully convey the scope of the invention to those skilled in the art.

Described herein are embodiments of systems and methods for generating nuclear magnetic resonance (NMR) well logs and water saturation ($S_w$) well logs for a well, and using the NMR and water saturation ($S_w$) well logs to determine reservoir free water level (FWL) and/or rock type. In some embodiments, a well is drilled (e.g., according to a pre-defined protocol) and logging is conducted to obtain NMR and water saturation ($S_w$) logs for the reservoir penetrated by the well. The logs may, then, be processed to determine the free water level (FWL) and/or rock type for the reservoir. For example, water saturation $T_2$ cutoff points are determined across a depth interval of interest (e.g., a targeted reservoir section) using the NMR and water saturation ($S_w$) logs, a subset of the water saturation $T_2$ cutoffs points that exhibit hyperbolic trend are selected, a theoretical water saturation ($S_w$) cutoff curve is generated using the subset of the water saturation ($S_w$) $T_2$ cutoff points (e.g., via curve fitting to the subset of points using two fitting parameters: a scaling factor (a) and a height above the FWL (HAFWL)), and the free water level (FWL) and/or rock type for the reservoir is determined using the theoretical water saturation ($S_w$) cutoff curve (e.g., using the determined scaling factor (a) and a $T_2$ value, e.g., based on a $T_2$ distribution of the NMR log, on the curve corresponding to a given depth and HAFWL). Accordingly, the free water level (FWL) and/or rock type for the reservoir can be determined using NMR and water saturation ($S_w$) logs for the well, without the use of a core-based PRT calibration. That is, the free water level (FWL) and/or rock type for the reservoir may be determined without engaging in coring processes that can be time consuming and expensive.

Fluid distribution within a porous medium can be driven by the relationship between the buoyancy pressure ($P_b$) exerted by the non-wetting fluid and the capillary pressure ($P_c$) that retains wetting fluid within the pores. In a water-wet reservoir rock any given pore can be considered water-filled if its threshold capillary pressure exceeds the hydrocarbon's buoyancy pressure ($P_b<P_c$). Conversely, it can be considered that hydrocarbon expels water from a pore when the hydrocarbon's buoyancy pressure overcomes the pore's threshold capillary pressure (e.g., $P_b>P_c$). The buoyancy pressure ($P_b$) may arise from the density difference between fluids as formulated based on Archimedes' principle as follows:

$$P_b=(\rho_w-\rho_o)\cdot g\cdot HAFWL, \quad (1)$$

where $\rho_w$ and $\rho_o$ are the densities of water and oil, respectively, g is the gravitational acceleration and HAFWL stands for the height above the free water level (FWL) in true vertical depth (TVD) (e.g., HAFWL=FWL−TVD). Buoyancy pressure ($P_b$) can be expressed as follows:

$$P_b=(G_w-G_o)\cdot HAFWL, \quad (2)$$

where the $G_w$ and $G_o$ are the water and hydrocarbon pressure gradients in pounds-per-square-inch per foot (psi/ft). Capillary pressure ($P_c$) within a porous medium can be expressed by the Young-Laplace equation as follows:

$$P_c=\sigma\cdot C, \quad (3)$$

where σ is the fluid interfacial tension and C is the curvature of the meniscus between the wetting and non-wetting fluids. The capillary pressure ($P_c$) for a capillary tube (a simple pore model) can be expressed as follows:

$$P_c = \frac{2\sigma\cos\theta}{r_t}, \quad (4)$$

where $r_t$ is the tube radius and θ is the solid surface-fluids contact angle. The contact angle may be dictated by surface wettability, being close to 0 degrees for strongly water wet systems and close to 180 degrees for strongly oil wet systems. Notably, capillary pressure ($P_c$) is inversely proportional to the pore size, as demonstrated by the above relationship between capillary pressure ($P_c$) and a tube radius ($r_t$) (which models pore size). That is, the smaller the pore size the higher the pressure that is required to expel the wetting fluid.

Considering at least equations 2 and 4, and the notion that a hydrocarbon expels water from a pore when the hydrocarbon's buoyancy pressure overcomes the pore's threshold capillary pressure (e.g., $P_b>P_c$), it can be determined that the fluid content of a capillary tube is dictated by its threshold pore size or radius ($r_{threshold}$), which corresponds to a point where the hydrocarbon's buoyancy pressure is about equal to the pore's capillary pressure (e.g., $P_b=P_c$). Thus, the threshold pore size ($r_{threshold}$) can be expressed as follows:

$$r_{threshold} = \frac{2\sigma\cos\theta}{(G_w - G_o)\cdot HAFWL} \quad (5)$$

Accordingly, a pore may be considered water-filled if its size ($r_t$) is less than the threshold pore size ($r_{threshold}$) at the level (e.g., $r_t<r_{threshold}$, thus $P_b<P_c$), and the pore may be considered hydrocarbon-filled if its size ($r_t$) is greater than the threshold pore size ($r_{threshold}$) at the level (e.g., $r_t>r_{threshold}$, thus $P_b>P_c$).

Figure 1B:
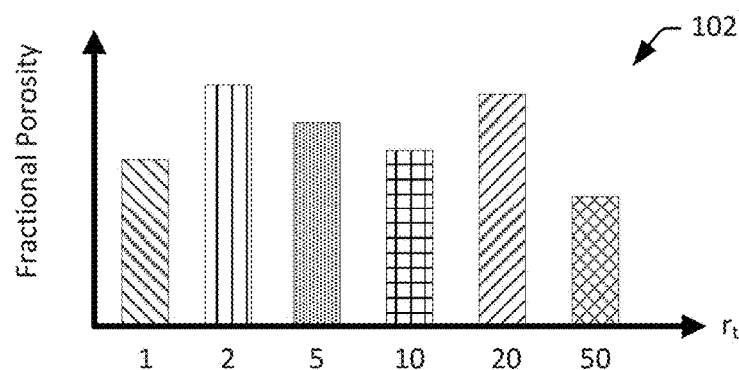
FIG. 1B is a pore-throat-size histogram in accordance with one or more embodiments.
Figure 1C:
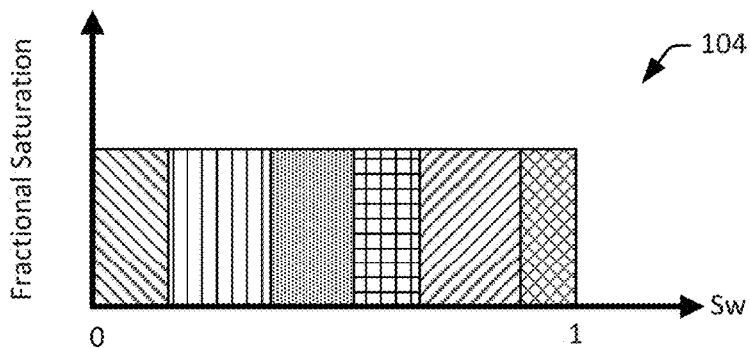
FIG. 1C is fractional wetting phase saturation diagram in accordance with one or more embodiments.

In some embodiments, porous rocks with multiple pore sizes contained therein can be represented as a bundle of capillary tubes with different sizes and volumes, as represented by FIGS. 1A-1C. FIG. 1A is diagram that illustrates a representation of a grouping of multiple pores 100 in accordance with one or more embodiments. More specifically, this diagram includes about eighteen different circles representing eighteen different pores 100 of various sizes. Pores having approximately the same size are shaded with a common pattern. As can be seen, each of the pores fall into one of six size groupings represented by common shading. FIG. 1B is a pore-throat-size histogram 102 in accordance with one or more embodiments. The histogram 102 corresponds to the pores 100 of FIG. 1A, and illustrates fractional porosity as a function of pore size (e.g., in microns) of the six size groupings. FIG. 1C is fractional wetting phase saturation diagram in accordance with one or more embodiments. The diagram 104 corresponds to the pores 100 of FIG. 1A, and illustrates fractional saturations of different pore sizes of the six size groupings.

Figure 2A:
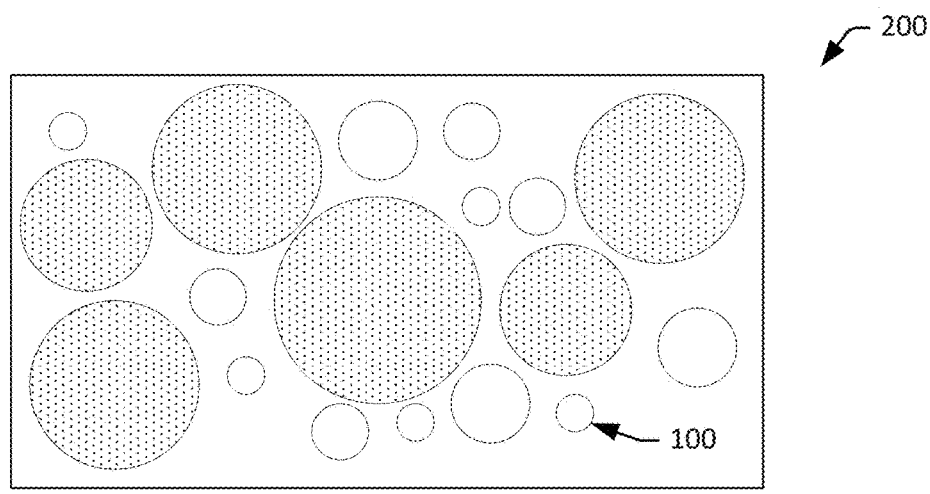
FIG. 2A is a diagram that illustrates a representation of water-filled pores and hydrocarbon-filled pores of a formation, marked by solid white and dotted circles, respectively, in accordance with one or more embodiments.
Figure 2B:
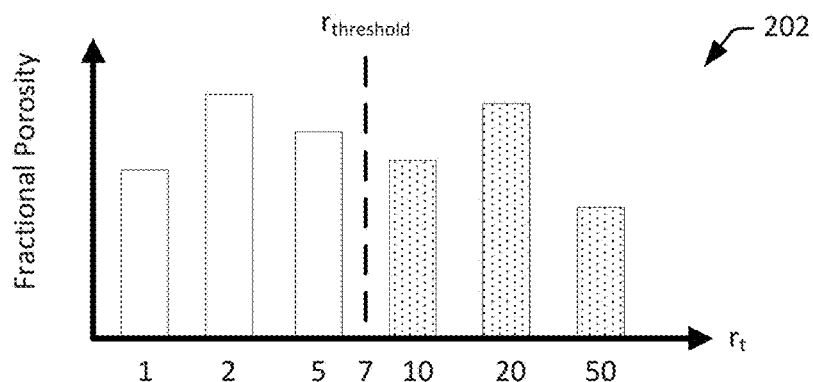
FIG. 2B is a pore-throat-size histogram diagram that represents water-filled pores and hydrocarbon-filled pores in accordance with one or more embodiments.
Figure 2C:
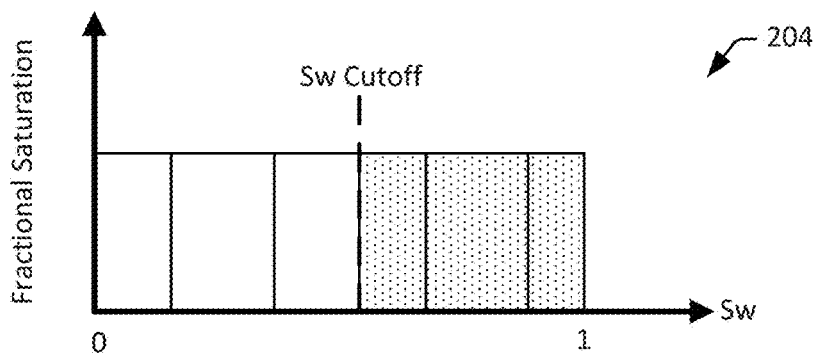
FIG. 2C is a fractional wetting phase saturation diagram that represents water-filled pores and hydrocarbon-filled pores in accordance with one or more embodiments.

As discussed above, for any given height above the free water level (HAFWL), all pores with a size ($r_t$) that is less than the threshold pore size ($r_{threshold}$) (e.g., $r_t < r_{threshold}$) can be considered to be water-filled, and all pores with a size ($r_t$) that is greater than the threshold pore size ($r_{threshold}$) (e.g., $r_t > r_{threshold}$) can be considered to be hydrocarbon-filled. The results of employing such a threshold are reflected in FIGS. 2A-2C. FIG. 2A is a diagram (similar to that of FIG. 1A) that illustrates water-filled pores 100 (e.g., pores with $r_t < r_{threshold}$) unshaded and the hydrocarbon-filled pores 100 (e.g., pores with $r_t > r_{threshold}$) in a shaded pattern. FIG. 2B is a pore-throat-size histogram diagram (similar to that of FIG. 1B) that further illustrates the location of the threshold pore size (e.g., $r_{threshold}$=7 microns) on the x-axis, and including the bars corresponding to the water-filled pores (e.g., pores with $r_t < r_{threshold}$) unshaded and the bars corresponding to the hydrocarbon-filled pores (e.g., pores with $r_t > r_{threshold}$) in a shaded pattern. FIG. 2C is a fractional wetting phase saturation diagram (similar to that of FIG. 1C) that further illustrates the bars corresponding to the water-filled pores (e.g., pores with $r_t < r_{threshold}$) unshaded and the bars corresponding to the hydrocarbon-filled pores (e.g., pores with $r_t > r_{threshold}$) in a shaded pattern.

Water-filled porosity ($\Phi_w$) can be determined as the summation of the porosity of all pores that are smaller than the threshold size, as represented by the following:

$$\Phi_w = \int_{r_t=0}^{r_{threshold}} P(r_t) dr_t \tag{6}$$

Similarly, hydrocarbon-filled porosity ($\Phi_o$) can be determined by the summation of the porosity for all pores that are equal to or larger than the threshold size, as represented by the following:

$$\Phi_o = \int_{r_t=r_{threshold}}^{\infty} P(r_t) dr_t \tag{7}$$

Fluid saturations, including water saturation ($S_w$) and oil saturation ($S_o$), can be obtained by a normalization to a total pore volume ($\Phi_T$), as represented by the following:

$$\Phi_T = \Phi_w + \Phi_o, \tag{8}$$

$$S_w = \frac{\Phi_w}{\Phi_w + \Phi_o}, \tag{9}$$

and $$S_o = \frac{\Phi_o}{\Phi_w + \Phi_o}, \tag{10}$$

Figures 3A, 3B:
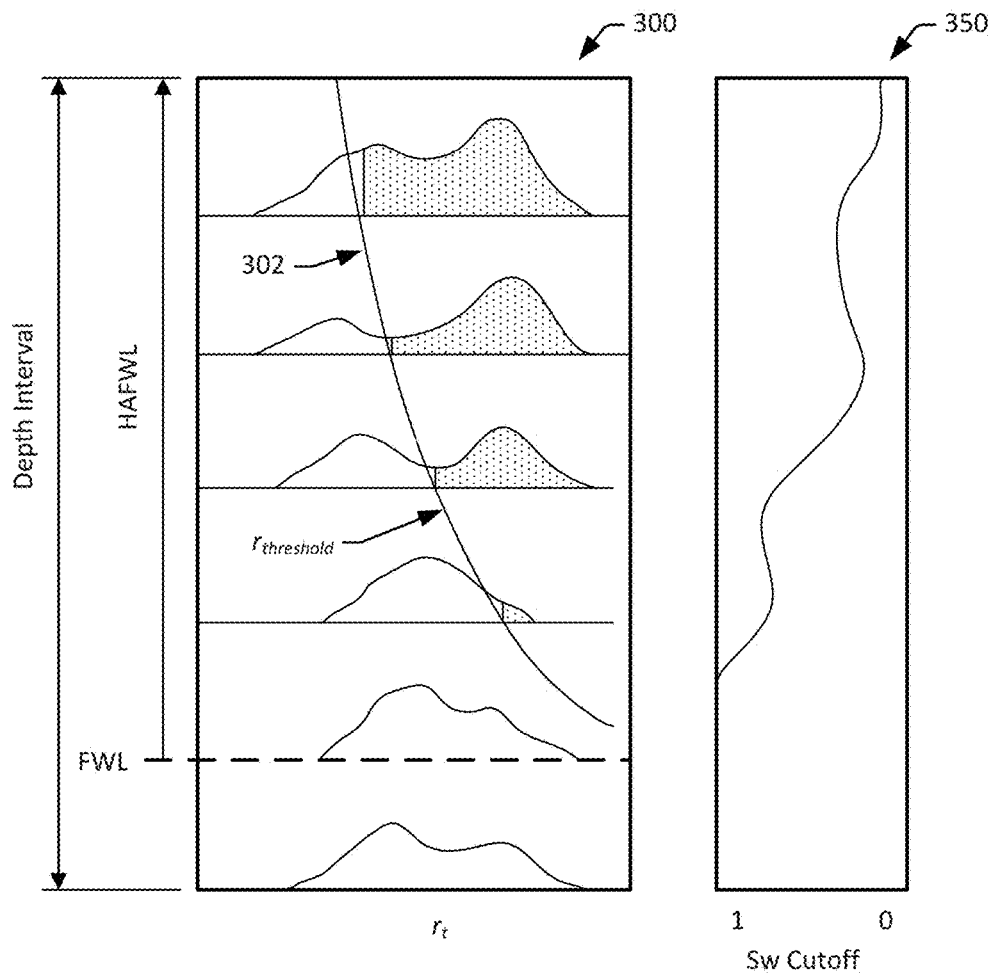
FIG. 3A is a diagram that illustrates application of a threshold pore size across a plurality of different depths in accordance with one or more embodiments.
FIG. 3B is a water saturation ($S_w$) log that corresponds to the diagram of FIG. 3A in accordance with one or more embodiments.

If the pore size histogram ($P(r_t)$), fluid densities, interfacial tension and contact angle are available as a function of TVD, then fluid distribution can be calculated by the above integration using a variable pore size cutoff and a given FWL as shown in FIG. 3A. FIG. 3A is a diagram 300 that illustrates application of a threshold pore size ($r_{threshold}$) across a plurality of different depths. For example, the diagram 300 includes a threshold size cutoff curve 302 that represents the varying value for threshold pore size ($r_{threshold}$) as a function of depth, and the application of the threshold pore size ($r_{threshold}$) for each of four depths above the FWL, as represented by the shaded portions of each of the histograms that represent hydrocarbon-filled pores at the corresponding depth/HAFWL and the unshaded portions of each of the histograms that represent water-filled pores at the corresponding depth/HAFWL. Although histograms for only a total of six depths (with five depths at or above the FWL) are shown for the purpose of illustration, a similar assessment can be made for each different depth. For example, a similar assessment could be made about every 0.1 m, 0.5 m, 1 m, 5 m, 10 m, 50 m or the like across a 100 m span (or depth interval) of the wellbore. FIG. 3B is a water saturation ($S_w$) log 350 that corresponds to the diagram 300 of FIG. 3A in accordance with one or more embodiments. For example, the water saturation ($S_w$) log 350 illustrates water saturation ($S_w$) vs depth, for the full depth interval represented by FIG. 3A. Notably, the cutoff attributable to threshold size ($r_{threshold}$) as a function of depth (TVD or HAFWL) may be a single hyperbolic curve if the interfacial tension, contact angle and fluid densities are constant across the depth interval of interest.

As noted above, NMR logs can provide insight into pore size. By the time-domain measurement of proton relaxation, NMR infers the degree of molecular interaction between fluid molecules (bulk relaxation mainly governed by viscosity), the interaction between the fluid and the pore surface (surface relaxation governed by pore size) and the fluid's ability to spread (diffusion relaxation governed by molecular diffusion). The decay rate of NMR relaxation, characterized by the NMR relaxation time $T_2$ can be simultaneously affected by these three mechanisms, as represented by the following:

$$\frac{1}{T_2} = \frac{1}{T_{2,bulk}} + \frac{1}{T_{2,surface}} + \frac{1}{T_{2,diffusion}} \tag{11}$$

The first term in the above equation 11 is the bulk relaxation time. This term is driven by the fluid's viscosity $\eta$, as demonstrated by the following:

$$\frac{1}{T_{2,bulk}} \sim \eta \tag{12}$$

With increasing viscosity the bulk relaxation becomes stronger, and in heavy oils the bulk relaxation can be the dominant relaxation mechanism.

The second term in the above equation 11 is the surface relaxation time. This term may depend on the specific surface area (S/V) of the pore, as demonstrated by the following:

$$\frac{1}{T_{2,surface}} = \xi_2 \frac{S}{V} = \xi_2 \cdot f_s \cdot \frac{1}{r_b}, \tag{13}$$

where $\xi_2$ is the NMR surface relaxivity, $f_s$ is the shape factor and $r_b$ is the pore body size. The NMR surface relaxivity ($\xi_2$) can be affected by the density of paramagnetic impurities on the pore surface which can vary with the rock's lithology. The shape factor $f_s$ relates the specific surface area with the characteristic dimension of pore body size ($r_b$). For example, for a capillary tube $f_s=2$, whereas for a sphere $f_s=3$.

The third term in the above equation 11 is the diffusion relaxation time. This term may depend on the fluid's self-diffusion $D_O$, as demonstrated by the following:

$$\frac{1}{T_{2,diffusion}} = D_0 \frac{(\gamma \cdot G \cdot TE)^2}{12}, \quad (14)$$

where $\gamma$ is the proton gyromagnetic ratio, G is the tool's permanent magnetic field gradient and TE is the NMR echo spacing.

For rock typing applications the relaxation rate may be dominated by surface relaxation, as demonstrated by the following relationship:

$$\frac{1}{T_{2,surface}} \gg \frac{1}{T_{2,bulk}} + \frac{1}{T_{2,diffusion}} \quad (15)$$

Based on the above, the measured $T_2$ can be approximated using the following relationship:

$$\frac{1}{T_2} \approx \frac{1}{T_{2,surface}}, \quad (16)$$

and the pore body size distribution can be represented by the NMR $T_2$ distribution as follows:

$$r_b = \xi_2 \cdot f_s \cdot T_2 \quad (17)$$

If NMR relaxation is dominated by surface relaxation, as described above, then a pore body to pore throat ratio ($\beta$) may be represented as follows:

$$\beta = \frac{r_b}{r_t}, \quad (18)$$

and can be used to obtain the following relationship:

$$r_t = \frac{\xi_2 \cdot f_s}{\beta} \cdot T_2, \text{ or} \quad (19)$$

$$T_2 = \frac{\beta}{\xi_2 \cdot f_s} \cdot r_t \quad (20)$$

Such linear relationships facilitate the usage of the NMR $T_2$ distribution for the purpose of saturation modeling as described earlier. The relationship provided above for threshold pore size ($r_{threshold}$) (e.g., in equation 5) can be substituted for threshold pore throat size ($r_t$) (e.g., in equation 20) to arrive at a relationship for $T_2$ cutoff, as represented by the following:

$$T_{2,cutoff} = \frac{\beta}{\xi_2 \cdot f_s} \cdot r_{threshold} = \frac{\beta}{\xi_2 \cdot f_s} \cdot \frac{2\sigma\cos\theta}{(G_w - G_o) \cdot HAFWL} = \frac{a}{HAFWL}, \quad (21)$$

where "a" is a scaling factor that is a function of rock surface properties (surface relaxivity), pore structure (pore shape, pore body/throat ratio), fluid properties (interfacial tension and densities), and interaction between fluid and solid surfaces (contact angle). The scaling factor (a) may be represented as follows:

$$a = \frac{\beta}{\xi_2 \cdot f_s} \cdot \frac{2\sigma\cos\theta}{(G_w - G_o)} \quad (22)$$

Figures 4A, 4B:
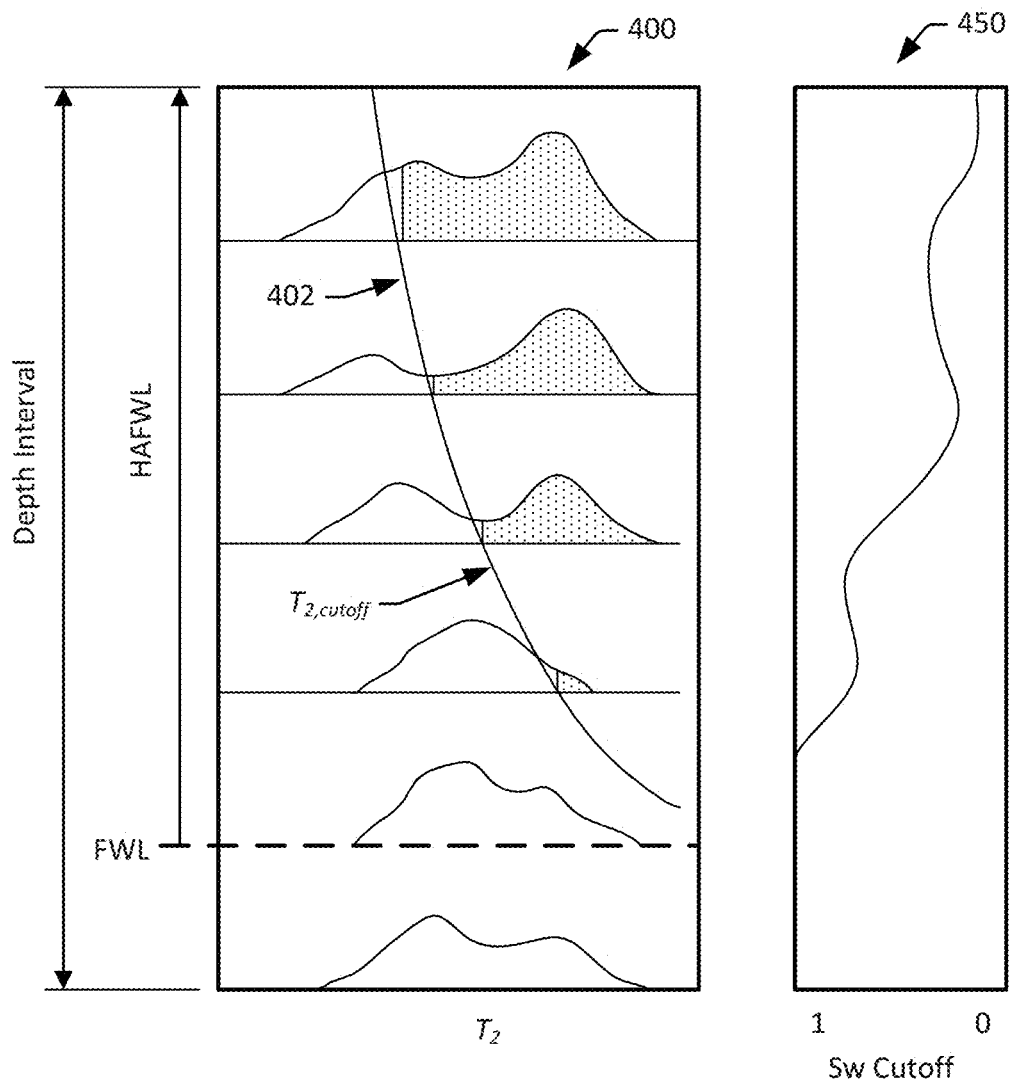
FIG. 4A is a diagram that illustrates the application of a $T_2$ cutoffs across a plurality of different depths in accordance with one or more embodiments.
FIG. 4B is a water saturation ($S_w$) log that corresponds to the diagram of FIG. 4A in accordance with one or more embodiments.
Figure 5:
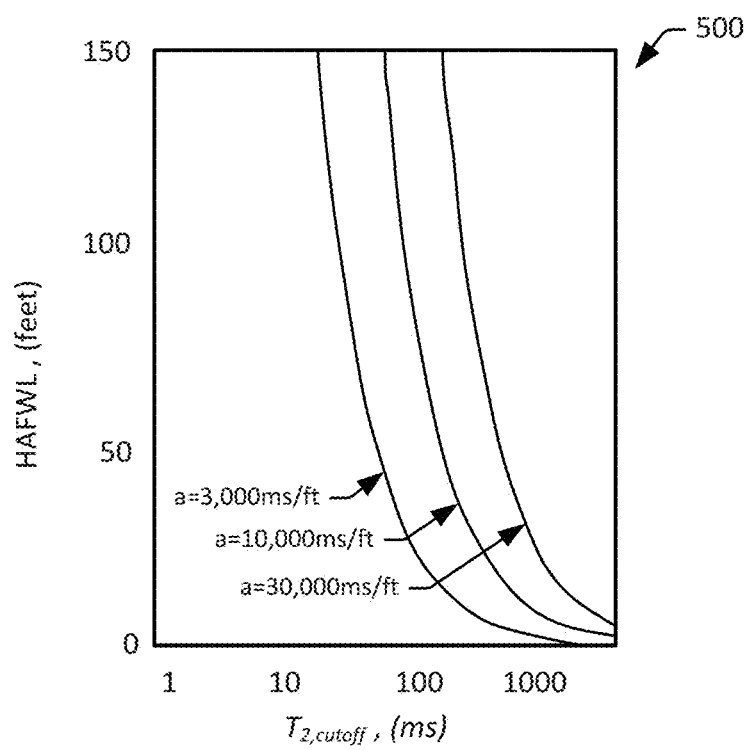
FIG. 5 is a plot that illustrates three realizations of the saturation cutoff with different scaling factors (a) in accordance with one or more embodiments.

Accordingly, fluid saturation can be calculated from the NMR $T_2$ array log using the variable $T_2$ cutoff as a function of HAFWL, as shown in FIGS. 4A and 4B. FIG. 4A is a diagram 400 that illustrates the application of a $T_2$ cutoff across a plurality of different depths. For example, the diagram 400 includes a $T_2$ cutoff curve 402 that represents the varying value for $T_2$ cutoff as a function of depth, and the application of the $T_2$ cutoff for each of four depths above the FWL, as represented by the shaded portions of each of the histograms that represent hydrocarbon-filled pores at the corresponding depth/HAFWL and the unshaded portions of each of the histograms that represent water-filled pores at the corresponding depth/HAFWL. Although histograms for only a total of six depths (with five depths at or above the FWL) are shown for the purpose of illustration, a similar assessment can be made for each different depth. For example, a similar assessment could be made about every 0.1 m, 0.5 m, 1 m, 5 m, 10 m, 50 m or the like across a 100 m span (or depth interval) of the wellbore. FIG. 4B is a water saturation ($S_w$) log 450 that corresponds to the plot of diagram 400 of FIG. 4A. For example, the water saturation ($S_w$) log 450 illustrates water saturation ($S_w$) vs depth, for the full depth range represented by FIG. 4A. Notably, the cutoff attributable to $T_2$ cutoff as a function of depth (TVD or HAFWL) is a single hyperbolic curve if the scaling factor (a) is constant in the interval of interest, or the following parameters are constant across the depth interval of interest: interfacial tension, contact angle, fluid densities, pore body to pore throat ratio (pore connectivity), NMR Surface relaxivity, and pore aspect ratio, or pore shape. In addition to the above it can also be assumed that the effects of bulk and diffusion relaxations are negligible compared to the surface relaxation. That is, it can be assumed that surface relaxation is the dominant mechanism. FIG. 5 is a plot 500 that illustrates three realizations of the saturation cutoff with different scaling factors (a) in accordance with one or more embodiments. The plot includes values for $T_2$ cutoff (ms) across a depth interval (0-150 ft above HAFWL) for three different values of the scaling factor (a) (e.g., a=3,000 ms/ft, a=10,000 ms/ft, and a=30,000 ms/ft). Notably, the curves exhibit hyperbolic shape similar to that in an NMR log presentation.

The simple representation of the scaling factor (a) can provide for a simple petrophysical reservoir typing (PRT) scheme: rocks with similar scaling factors values (a) can be construed as being in a given petrophysical reservoir type (PRT). That is, for example, reservoirs with similar rock surface properties, pore structure, and fluid properties can be grouped together based on their having similar value scaling factors (a). In accordance with this PRT scheme, rocks with different pore volumes, pore sizes, and fluid properties may fit in one PRT based on their having similar value scaling factors (a). Thus, even complex pore systems, such as carbonates, can be modeled accurately with only a few different reservoir types. Moreover, the simple shape of the theoretical cutoff curve (e.g., curve 402) within a PRT enables a determination of the FWL by combining NMR and water saturation ($S_w$) logs as discussed below.

In some embodiments, the free water level (FWL) for reservoir penetrated by a well can be determined from NMR logs and water saturation ($S_w$) logs for the well. Such a process can generally include drilling a well and obtaining an NMR and water saturation ($S_w$) logs for the well (in accordance with a specified protocol), and performing the following operations using the logs: (1) calculating the saturation $T_2$ cutoff points from the obtained NMR and uninvaded reservoir water saturation ($S_w$) logs; (2) selecting a subset of water saturation ($S_w$) cutoff points that follow a hyperbolic trend; and (3) generating a theoretical water saturation ($S_w$) cutoff curve using the subset of the water saturation ($S_w$) $T_2$ cutoffs; and (4) determining free water level (FWL) and rock type for the reservoir using the theoretical water saturation ($S_w$) cutoff curve.

In some embodiments, drilling of a well may be conducted in response to determining that some of all of the following conditions are satisfied:

1. The rock is water-wet in the shallow flushed zone (e.g., 2-10 cm (about 1-4 inches) from the borehole);
2. The rock uniformly water-filled in the shallow flushed zone;
3. There is no extreme deep invasion that affects deep resistivity (Rt) measurements;
4. There is no solids invasion to distort surface relaxation measurements; and
5. There are no large borehole irregularities such as washouts or rugosity to distort NMR and triple combo logs.

With regard to the first condition, water-wetting in the shallow flushed zone may be achieved naturally or by adding surfactants to the drilling mud such that the water-based mud filtrate and/or formation water contacts the rock surface. Under these conditions, NMR surface relaxation translates to pore size as described by Equation (13). With regard to the second condition, rock uniformly water-filled in the shallow flushed zone may be achieved by drilling with mud weights to ensure steady overbalance.

In some instances, the uninvaded water-saturation can be accurately determined if (a) the sensitive volume of saturation log is deep enough to reach the uninvaded zone, and (b) the petrophysical model that translate the saturation log response to water saturation is accurate. Saturation logs can include deep resistivity (e.g., with the knowledge of formation water resistivity ($R_w$) and formation parameters such as cementation and saturation exponents), and/or pulsed neutron spectroscopy or capture sigma measurements (e.g., with a knowledge of lithology, porosity and formation oil and water properties).

In some embodiments, NMR logging includes employing the following:

1. Full polarization (i.e. using a long wait-time, TW)
2. Large number of echoes to ensure proper resolution of large pores
3. Small echo spacing (TE) to accentuate surface relaxation by minimizing diffusion effects.

With regard to tool deployment, wireline logs (e.g., sensors being lowered into the borehole after drilling the well) may be employed. This can be advantageous from the standpoint of mud filtrate flushing and logging conditions. Notably, in some instances, logging-while-drilling (LWD) logs may encounter better shaped boreholes and the risk of deep invasion affecting deep-reading tools is minimal. If geosteering is required then, LWD may be employed as the mode of operation.

In some embodiments, drilling a well (in accordance with a specified protocol) includes the following: (1) adding surfactant to a water-based mud (WBM) used in the drilling process, including the drilling of the targeted reservoir section (e.g., the depth interval), to facilitate close to zero interfacial tension to maximize sweep in a flushed zone, thereby enhancing $P(r_t)$; and/or (2) drilling the targeted reservoir section (e.g., the depth interval) with steady overbalance pressure to have consistent mud filtrate flushing. In some embodiments, obtaining an NMR and water saturation ($S_w$) logs for the well (in accordance with a specified protocol) includes the following: (1) acquiring triple combo logs and perform porosity and uninvaded reservoir water saturation analysis; and/or (2) obtaining NMR logs with minimum TE and large number of echoes and/or a short echo spacing (e.g., the shortest possible echo spacing) (or, alternatively, $T_1$ log may be run with a large number of different wait-times). A large number of echoes may ensure good spectral resolution at high $T_2$ values. Short echo spacing may reduce diffusion effects. The NMR logging may be conducted with a relatively high NMR signal-to-noise ratio as peak broadening due to excessive regularization may mask fine rock type variations.

Figure 6:
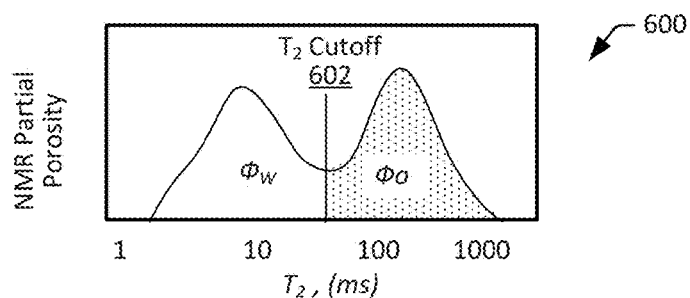
FIG. 6 is a diagram that illustrates the location of a determined $T_2$ cutoff for a given depth overlaid on a histogram of NMR partial porosity for the depth in accordance with one or more embodiments.
Figure 7A:
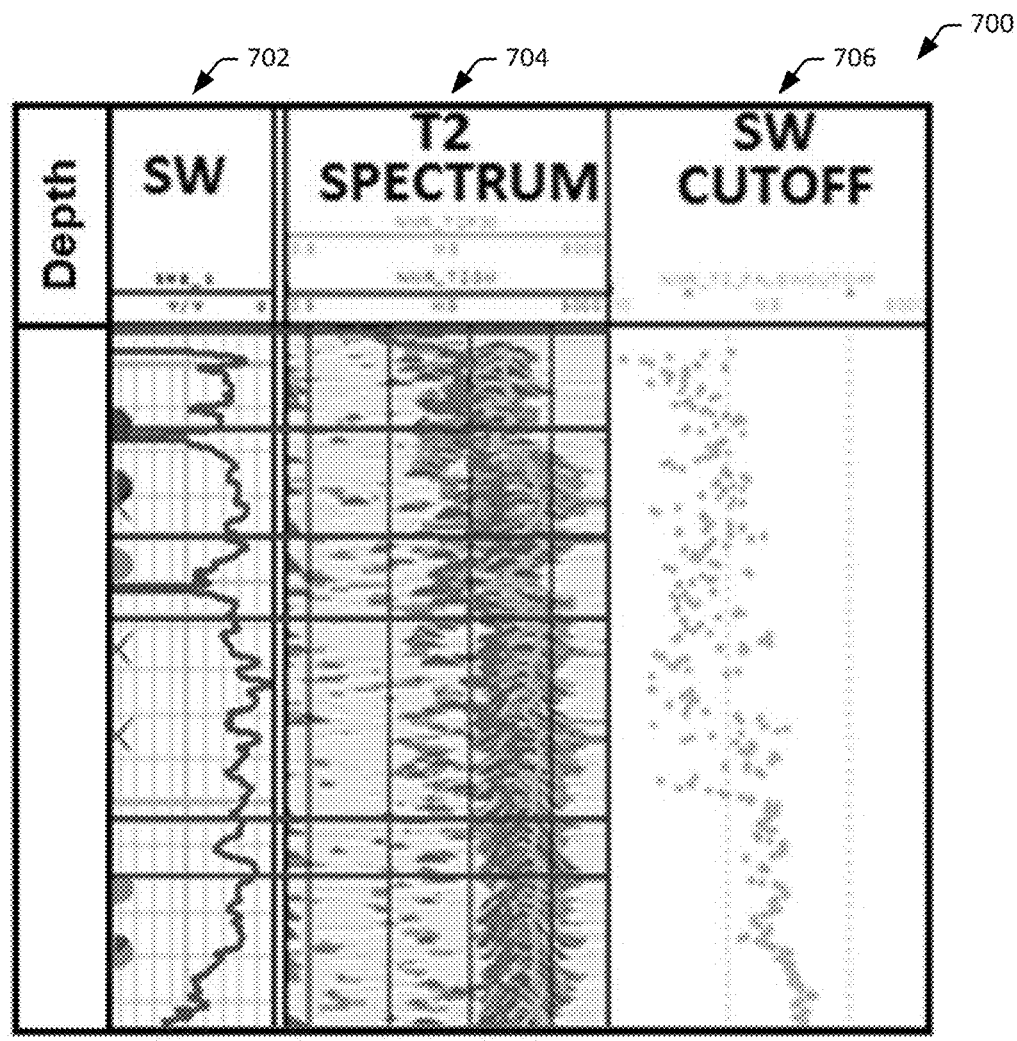
FIGS. 7A-7C are illustrations of an example combined log for a well in accordance with one or more embodiments.

The first step of the analysis of the logs (e.g., calculating the saturation $T_2$ cutoff points from the obtained NMR and uninvaded reservoir water saturation ($S_w$) logs), can include, for each depth level, back calculation of the saturation $T_2$ cutoff from an NMR and uninvaded reservoir water saturation ($S_w$) log. This may include adjusting the $T_2$ cutoff for a given depth to the time at which the water-filled and hydrocarbon-filled porosities for that depth match the input water saturation ($S_w$) for that depth (e.g., as defined by equation 9). FIG. 6 is a diagram 600 that illustrates the location of a determined $T_2$ cutoff 602 for a given depth overlaid on a histogram of NMR partial porosity for the depth in accordance with one or more embodiments. The $T_2$ cutoff is located at about 60 ms, the shaded portion of the histogram (to the right of the $T_2$ cutoff) represents hydrocarbon-filled pores at the corresponding depth (or HAFWL) and the unshaded portion the histogram (to the left of the $T_2$ cutoff) represents water-filled pores at the corresponding depth (or HAFWL). Although FIG. 6 represents a histogram for a single depth (or HAFWL) for the purpose of illustration, a similar assessment can be made for different depths. For example, a similar assessment could be made about every 0.1 m, 0.5 m, 1 m, 5 m, 10 m, 50 m or the like across a 100 m span (or depth interval) of the wellbore. FIG. 7A is an example combined log 700 for a well that illustrates water saturation ($S_w$) cutoffs determined across a depth interval for a well in accordance with one or more embodiments. The combined log 700 includes an uninvaded reservoir water saturation ($S_w$) log 702 for the depth interval, an NMR (T2 spectrum) log 704 for the depth interval, and a corresponding cutoff log ($S_w$ Cutoff) 706 for the depth interval. Each point in the cutoff log ($S_w$ Cutoff) 706 represents a $T_2$ cutoff determined for a given depth based on the corresponding water saturation ($S_w$) specified by the water saturation ($S_w$) log 702 for the depth, and the corresponding $T_2$ specified by the NMR (T2 spectrum) log 704 for the depth. Accordingly, the $T_2$ cutoffs for the well are determined based on the water saturation ($S_w$) log 702 for the well and the NMR (T2 spectrum) log 704 for the well. Notably, at shallower depths, there is a considerable scatter in the $T_2$ cutoff values that can be attributed to low water saturations and generally higher noise in the short $T_2$ part of the NMR log 704. The scatter diminishes toward the bottom of the depth interval. This diminished scatter may be attributed to the higher water content and possibly a lesser degree of reservoir type variations at greater depths.

Figure 7B:
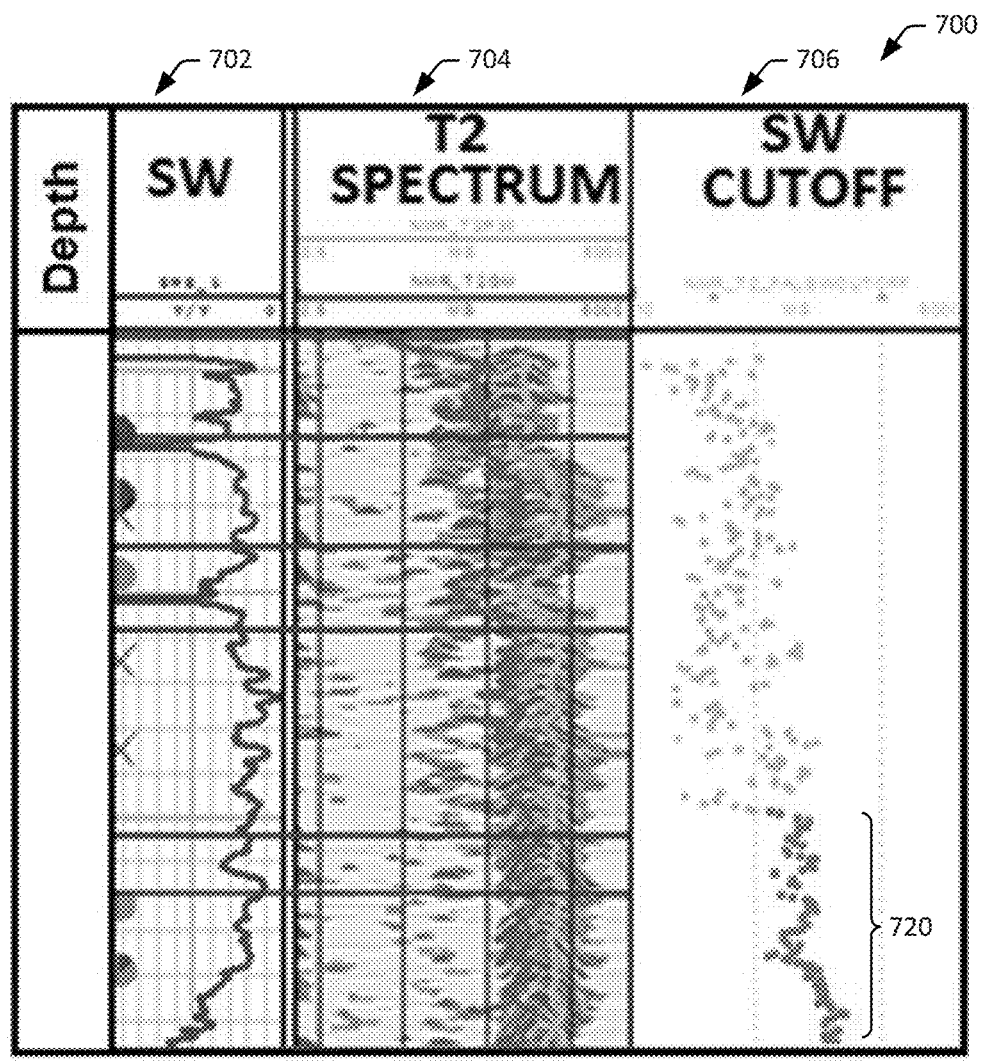

The second step of the analysis of the logs (e.g., selecting a subset of water saturation ($S_w$) cutoff points that follow a hyperbolic trend), can include selecting a subset of the $T_2$ cutoff points (determined in the first step) that correspond to a hyperbolic trend. Continuing with the example combined log 700 illustrated in FIG. 7A, this can include, for example, selecting a subset of points toward the bottom of the depth interval, where scatter is diminished and a relatively clearly hyperbolic trend is present. FIG. 7B illustrates a subset of $T_2$ cutoff points 720 of the combined log 700 in accordance with one or more embodiments. The subset of $T_2$ cutoff points 720 (relatively dark in color) may include a set of $T_2$ cutoff points contained in the depth interval that exhibit a hyperbolic trend.

Figure 7C:
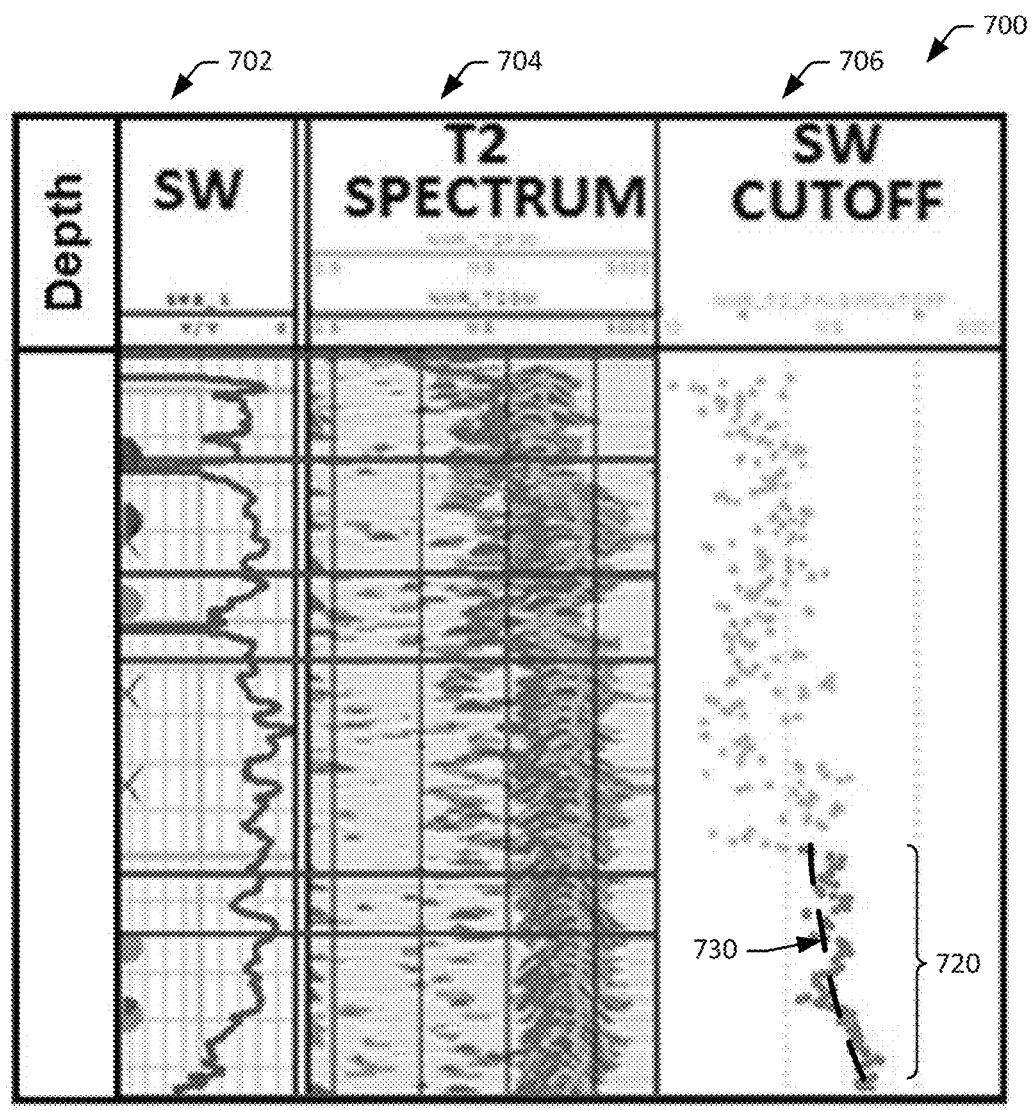

The third step of the analysis of the logs (e.g., generating a theoretical water saturation ($S_w$) cutoff curve using the subset of the water saturation ($S_w$) $T_2$ cutoffs), can include conducting a curve fitting to generate a theoretical water saturation ($S_w$) cutoff curve to approximate the hyperbolic trend exhibited by the subset of $T_2$ cutoff values 720. This can include fitting based on two fitting parameters: the scaling factor (a) and the HAFWL (or FWL where the depth for each $T_2$ cutoff values 720 and the FWL are expressed as a TVD). FIG. 7C illustrates a theoretical water saturation ($S_w$) cutoff curve 730, fit to the $T_2$ cutoff values 720 of the combined log 700 in accordance with one or more embodiments. Thus, this theoretical water saturation ($S_w$) cutoff curve 730 may have an associated value for the scaling factor (a) for any given depth above the FWL. Using the relationship of $T_2$ cutoff to the scaling factor (a) and HAFWL (e.g., expressed in equation 21), the HAFWL for a given depth can be determined by the following relationship:

$$HAFWL_{depth} = \frac{a}{T_{2,cutoff,depth}}, \tag{23}$$

where $T_{2,cutoff,depth}$ is a theoretical $T_2$ cutoff value determined for a given depth using theoretical water saturation ($S_w$) cutoff curve, a is the scaling factor determined for the theoretical water saturation ($S_w$) cutoff curve, and $HAFWL_{depth}$ is the distance of the given depth above the FWL. The FWL may be the true vertical depth (TVD) of a given point plus the HAFWL determined for the given point. Thus, FWL may be expressed as follows:

$$FWL = HAFWL_{depth} + TVD_{depth}, \tag{24}$$

where $HAFWL_{depth}$ is the distance of a given point above the FWL (e.g., determined based on a theoretical water saturation ($S_w$) cutoff curve and the relationship of equation 23), and $TVD_{depth}$ is the true vertical depth of the point. Thus, for example, if a is determined to have a value of about 1,000 ms/m for a theoretical water saturation ($S_w$) cutoff curve, and the curve indicates a $T_2$ value of about 50 ms/m² ($T_{2,cutoff}$=50 ms/m²) for a depth of about 1000 m (TVD=1000 m), then (applying equation 23) the HAFWL may be determined to be about 20 m (e.g., 1000 ms/m/50 ms/m²=20 m) for the depth of 1000 m, and (applying equation 24) the FWL may be determined to be at a true vertical depth of about 1020 m (e.g., 1000 m+20 m=1020 m). In some embodiments, a rock type for the formation can be determined as a rock type that is associated with the scaling factor (a). Continuing with the above example, the rock type for the depth interval and/or the reservoir penetrated by the well may be determined to be a rock type associated with the scaling factor value of about 1,000 ms/m. In some embodiments, a rock type (or reservoir type) encompasses some or all of different types of rocks having similar scaling factors (a). This can represent a combination of the density contrast and interfacial tension between formation water and hydrocarbons and the size and connectivity of pores within the rock of the reservoir. This can be related to the "other classifications" of reservoir rocks and the history of fluid movement therein. Examples of other classifications include rock descriptions such as Dunham, Hagerty-Cantrell, Lucia, Thomeer, and Leverett J-function classifications for carbonates or petrophysical rock typing driven by core description, petrography, and/or core analysis (porosity, permeability, NMR with 100% water saturation, or mercury-injection porosimetry measurements.

In some embodiments, a "best fit" theoretical water saturation ($S_w$) cutoff curve 730 can be determined for a set of $T_2$ cutoff values 720 via a fitting operation that includes minimizing the distance between the theoretical and measured $T_2$ cutoffs in a logarithmic space. Such a fitting operation may be expressed as follows:

$$\min_{a,FWL}\{\Sigma_{i=1}^{N}[\log(T_{2,cutoff,i}^{measured})-\log(T_{2,cutoff,i}^{theoretical})]^2\} \tag{25}$$

In some embodiments, a "best fit" theoretical water saturation ($S_w$) cutoff curve 730 can be determined for a set of $T_2$ cutoff values 720 via a fitting operation that includes minimizing the distance between the measured water saturation (Sw) and that calculated using the theoretical cutoffs. Such a fitting operation may be expressed as follows:

$$\min_{a,FWL}\{\Sigma_{i=1}^{N}[Sw_i^{measured}-Sw(T_{2,cutoff,i}^{theoretical})]^2\} \tag{26}$$

In some embodiments, a "best fit" theoretical water saturation ($S_w$) cutoff curve 730 can be determined for a set of $T_2$ cutoff values 720 via a fitting operation that includes minimizing the distance between the measured bulk water volume and that calculated using the theoretical cutoffs. Such a fitting operation may be expressed as follows:

$$\min_{a,FWL}\{\Sigma_{i=1}^{N}[BVw_i^{measured}-BVw(T_{2,cutoff,i}^{theoretical})]^2\} \tag{27}$$

Figure 8:
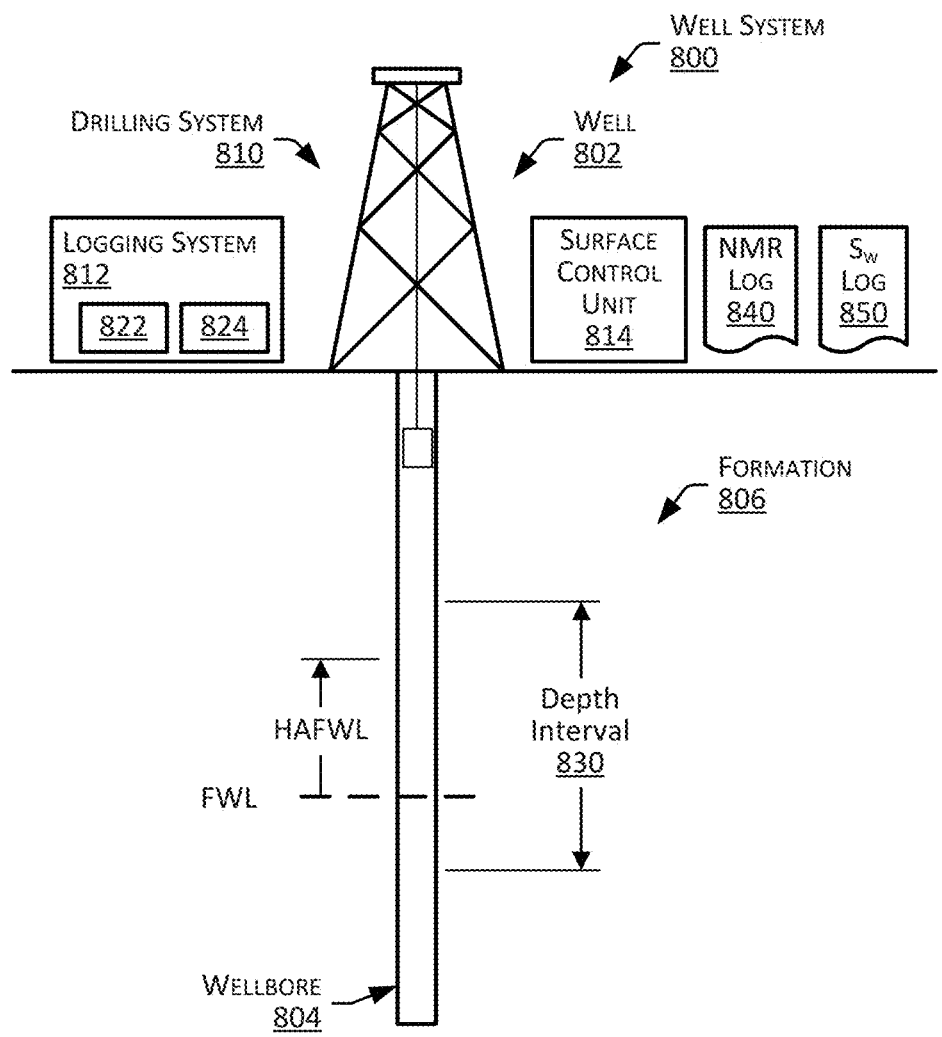
FIG. 8 is a diagram that illustrates a well environment in accordance with one or more embodiments.

FIG. 8 is a diagram that illustrates a well system 800 in accordance with one or more embodiments. The well environment 800 can include a well 802 having a wellbore 804 extending into a formation 806. The formation 806 may have a free water level (FWL) at a given true vertical depth (TVD) from the surface. The FWL may initially be unknown, but may be determined using the techniques described herein.

The well system 800 may include a drilling system 810, a logging system 812, and a surface control unit 814. The drilling system 810 may include a drill string, drill bit, a mud circulation system and/or the like for use in boring the wellbore 804 into the formation 806. The logging system 812 may include one or more logging tools, such as a NMR logging tool 822 and/or a resistivity logging tool 824, for use in logging various characteristics of the well 802, such as formation porosity, formation permeability, resistivity, water saturation, and the like. For example, the NMR logging tool 822 may be lowered into the wellbore 804 to take NMR measurements as it traverses a depth interval 830 (e.g., targeted reservoir section) of the wellbore 804. The resulting NMR measurements may be stored and/or processed, for example, by the surface control unit 814, to generate a corresponding NMR log 840 for the well 802. The NMR log 840 may include, for example, a plot of $T_2$ response time vs TVD across the depth interval 830 of the wellbore 804. Similarly, the resistivity logging tool 824 may be lowered into the wellbore 804 to take resistivity measurements as it traverses the depth interval 830 of the wellbore 804. The resulting resistivity measurements may be stored and/or processed, for example, by the surface control unit 814, to generate a corresponding water saturation ($S_w$) log 850 for the well 802. As described herein, in some embodiments, well logs, such as NMR log 840 and water saturation ($S_w$) log 850 can be used to determine characteristics of the well 802, such as the FWL and/or rock type for the formation 806 (e.g., the reservoir penetrated by the well). For example, as described herein, the NMR log 840 and the water saturation ($S_w$) log 850 for the formation 806 across the depth interval 830 of the wellbore 804 can be used to calculate saturation $T_2$ cutoff points for the depth interval 830, a subset of the water saturation ($S_w$) cutoff points that follow a hyperbolic trend can be identified, a curve fitting operation can be conducted using the subset of measured $S_w$ cutoff points to generate a theoretical water saturation ($S_w$) cutoff curve, and the theoretical water saturation ($S_w$) cutoff curve can be used to determine the FWL and rock type for the well 802. In some embodiments, such processing can be provided by the surface control unit 814. In some embodiments, the surface control unit 814 may be a computer or control system that is the same or similar to the computer/control system 1000 described below with regard to FIG. 10.

Figure 9:
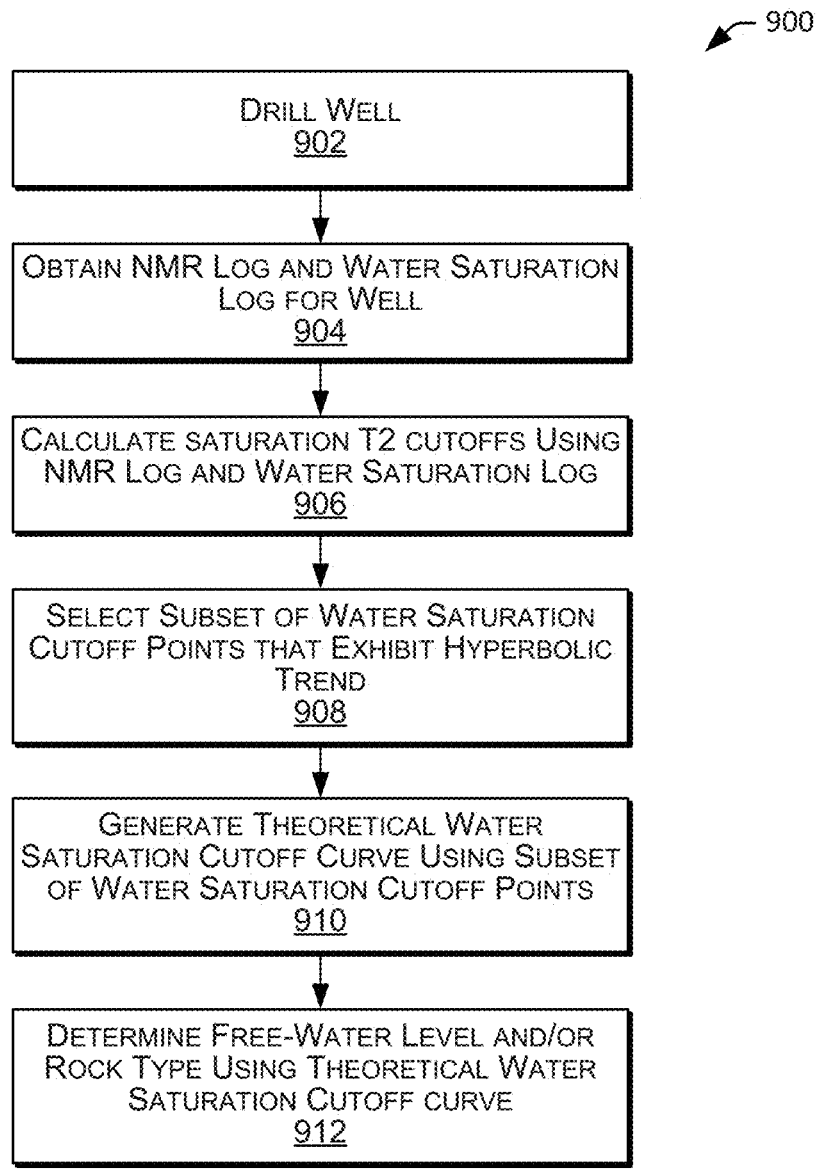
FIG. 9 is a flowchart that illustrates a method for determining well characteristics in accordance with one or more embodiments.

FIG. 9 is a flowchart that illustrates a method 900 for determining well characteristics in accordance with one or more embodiments. The well characteristics may include FWL and rock type for the well (e.g., the FWL and rock type of the reservoir penetrated by the well), and the method 900 may include using NMR and water saturation ($S_w$) logs for the well to determine the well characteristics. Method 900 may generally include, drilling a well (block 902), obtaining an NMR log and water saturation ($S_w$) log for the well (block 904), calculating water saturation $T_2$ cutoffs using the NMR log and the water saturation logs (block 906), selecting a subset of the water saturation ($S_w$) $T_2$ cutoffs that exhibit hyperbolic trend (block 908), generating a theoretical water saturation ($S_w$) cutoff curve using the subset of the water saturation ($S_w$) $T_2$ cutoffs (block 910), and determining free water level (FWL) and rock type for the well using the theoretical water saturation ($S_w$) cutoff curve (block 912).

In some embodiments, drilling a well (block 902) includes drilling a well 802 in accordance with one or more predefined protocols. Drilling a well can include employing some or all of the drilling techniques described herein. For example, drilling a well may include (at least while drilling the depth interval 830 of the wellbore 804) adding surfactant to a water-based mud (WBM) used in the drilling process and/or drilling with steady overbalance pressure to have consistent mud filtrate flushing. This can, for example, facilitate close to zero interfacial tension to maximize sweep in a flushed zone, thereby enhancing porosity ($P(r_t)$).

In some embodiments, obtaining an NMR log and water saturation ($S_w$) log for the well (block 904) includes obtaining an NMR log of the well 802 and/or an uninvaded water saturation ($S_w$) log for the well 802. NMR logging can include employing some or all of the NMR logging techniques described herein. With regard to the NMR log, for example, the NMR logging tool 822 may be lowered into the wellbore 804 to obtain NMR measurements (e.g., including T2 response times) of the formation 806 across at least the depth interval 830 of the wellbore 804. The NMR measurements may be provided from the NMR logging tool 822 to the surface control unit 814, and the surface control unit 814 may process the NMR measurements to generate a corresponding NMR log 840 for the depth interval 830. In some embodiments, the NMR logging may be completed according to a specified protocol. For example, the NMR logging may be accomplished using a minimum TE and large number of echoes and/or a short echo spacing (e.g., the shortest possible echo spacing) (or, alternatively, $T_1$ log may be run with a large number of different wait-times). With regard to the water saturation ($S_w$) log, for example, the resistivity logging tool 824 may be lowered into the wellbore 804 to obtain resistivity measurement for the formation 806 across at least the depth interval 830 of the wellbore 804. The resistivity measurements may be provided from the resistivity logging tool 824 to the surface control unit 814, and the surface control unit 814 may process the resistivity measurements to generate a corresponding water saturation ($S_w$) log 850 for the depth interval 830.

In some embodiments, calculating water saturation $T_2$ cutoffs using the NMR log and the water saturation logs (block 906) includes, for each or a plurality of depth levels in a depth interval of interest, back-calculating the saturation $T_2$ cutoff points from the obtained NMR log 840 and the obtained uninvaded reservoir water saturation ($S_w$) log 850. For example, the surface control unit 814 may, for each 0.5 m depth increment of the depth interval 830 represented by the NMR log 840 and the reservoir water saturation ($S_w$) log 850, back-calculate the saturation $T_2$ cutoff from the NMR log 840 and the reservoir water saturation ($S_w$) log 850. This may include determining the $T_2$ cutoff for a given depth to be the time at which the water-filled and hydrocarbon-filled porosities for that depth match the input water saturation ($S_w$) for that depth. The depth interval of interest may be a depth interval that covers a transition zone in which the water saturation significantly varies with depth. For an FWL optimization process, the lower and upper boundaries of the depth interval of interest may be defined by the lower and upper boundaries of the depth interval within which a search for the FWL is performed. FIG. 6 is a diagram 600 that illustrates the location of a determined $T_2$ cutoff 602 for a given depth overlaid on a histogram of NMR partial porosity for the depth 604 in accordance with one or more embodiments. The $T_2$ cutoff is located at about 60 ms, the shaded portion of the histogram (to the right of the $T_2$ cutoff) represents hydrocarbon-filled pores at the corresponding depth (or HAFWL) and the unshaded portion the histogram (to the left of the $T_2$ cutoff) represents water-filled pores at the corresponding depth (or HAFWL). Although FIG. 6 represents a histogram for a single depth (or HAFWL) for the purpose of illustration, a similar assessment can be made for different depths. For example, if the depth interval 830 of the wellbore 804 is about 100 m, a similar assessment could be made about every 0.5 m across the depth interval 830, for a determination of about 200 individual cutoff points. FIG. 7A is an example combined log 700 for a well that illustrates water saturation ($S_w$) cutoffs determined across a depth interval for a well in accordance with one or more embodiments. The combined log 700 includes an uninvaded reservoir water saturation ($S_w$) log 702 for the depth interval, an NMR (T2 spectrum) log 704 for the depth interval, and a corresponding cutoff log ($S_w$ Cutoff) 706 for the depth interval. Each point in the cutoff log ($S_w$ Cutoff) 706 represents a $T_2$ cutoff determined for a given depth based on the corresponding water saturation ($S_w$) specified by the water saturation ($S_w$) log 702 for the well, and the corresponding T2 specified by the NMR (T2 spectrum) log 704 for the well.

In some embodiments, selecting a subset of the water saturation ($S_w$) $T_2$ cutoffs that exhibit hyperbolic trend (block 908) includes identifying a subset of the determined $T_2$ cutoff points across a given subset of the interval of interest that exhibit a hyperbolic trend. Continuing with the above example, if the last 20 points of the about 200 individual cutoff points determined (e.g., across about the last 10 m of the depth interval 830) exhibit a hyperbolic trend, the surface control unit 814 may identify those 20 points as a subset of the water saturation ($S_w$) $T_2$ cutoffs. FIG. 7B illustrates a subset of $T_2$ cutoff values 720 of the combined log 700 that may be selected in accordance with one or more embodiments.

In some embodiments, generating a theoretical water saturation ($S_w$) cutoff curve using the subset of the water saturation ($S_w$) $T_2$ cutoffs (block 910) includes conducting a curve fitting to generate a theoretical water saturation ($S_w$) cutoff curve to approximate the hyperbolic trend exhibited by the subset of $T_2$ cutoff values 720. This can include fitting based on two fitting parameters: the scaling factor (a) and the HAFWL (or FWL where the depth for each $T_2$ cutoff values 720 and the FWL are expressed as a TVD). Continuing with the above example, the surface control unit 814 may generate a theoretical water saturation ($S_w$) cutoff curve based on a fitting to the 20 points identified as a subset of the water saturation ($S_w$) $T_2$ cutoffs. Accordingly, the surface control unit 814 may determine a value for the scaling factor (a) (e.g., a=1,000 ms/m) that corresponds to the theoretical water saturation ($S_w$) cutoff curve. In some embodiments, a "best fit" theoretical water saturation ($S_w$) cutoff curve 730 can be determined for a set of $T_2$ cutoff values 720 via a fitting operation that includes minimizing the distance between the theoretical and measured $T_2$ cutoffs in a logarithmic space. In some embodiments, a "best fit" theoretical water saturation ($S_w$) cutoff curve 730 can be determined for a set of $T_2$ cutoff values 720 via a fitting operation that includes minimizing the distance between the measured water saturation (Sw) and that calculated using the theoretical cutoffs. In some embodiments, a "best fit" theoretical water saturation ($S_w$) cutoff curve 730 can be determined for a set of $T_2$ cutoff values 720 via a fitting operation that includes minimizing the distance between the measured bulk water volume and that calculated using the theoretical cutoffs. FIG. 7C illustrates a theoretical water saturation ($S_w$) cutoff curve 730 fit to the $T_2$ cutoff values 720 of the combined log 700 in accordance with one or more embodiments.

In some embodiments, determining free water level (FWL) and rock type for the well using the theoretical water saturation ($S_w$) cutoff curve (block 912) includes determining the FWL and/or a rock type for the well 802 using the scaling factor (a). For example, using the scaling factor (a) for the determined theoretical water saturation ($S_w$) cutoff curve, the surface control unit 814 may determine, for a given point/depth on the curve, a corresponding HAFWL, and combine that HAFWL and the depth of the point to determine the FWL. Continuing with the above example, if a is determined to have a value of about 1,000 ms/m for a theoretical water saturation ($S_w$) cutoff curve, and the curve indicates a $T_2$ value of about 50 ms/m$^2$ ($T_{2,cutoff}$=50 ms/m$^2$) for a depth of about 1000 m (TVD=1000 m), then (applying equation 23) the HAFWL may be determined to be about 20 m (e.g., 1000 ms/m/50 ms/m$^2$=00 m) for the depth of 1000 m, and (applying equation 24) the FWL may be determined to be at a true vertical depth of about 1020 m (e.g., 1000 m+20 m=1020 m). In some embodiments, a rock type for the formation can be determined as a rock type that is associated with the scaling factor (a). Continuing with the above example, the rock type for the depth interval and/or the well may be determined to be a rock type associated with the scaling factor value of about 1,000 ms/m. In some embodiments, the determined well characteristics (e.g., FWL, rock type, and the like) may be stored and/or presented for viewing by a user (e.g., via graphical user interface) and/or can be used in making determinations regarding operation of the well (e.g., including drilling, logging and/or productions operations). Accordingly, FWL and/or rock type can be determined by calculating saturation $T_2$ cutoffs from NMR and water saturation logs. Thus, it may not be necessary to conduct a rigorous core-based PRT calibration, thereby, potentially eliminating the need of core analysis and the procedure. The determination of FWL and/or rock type from NMR and water saturation logs can be applied as soon as NMR and water saturation logs are available.

Figure 10:
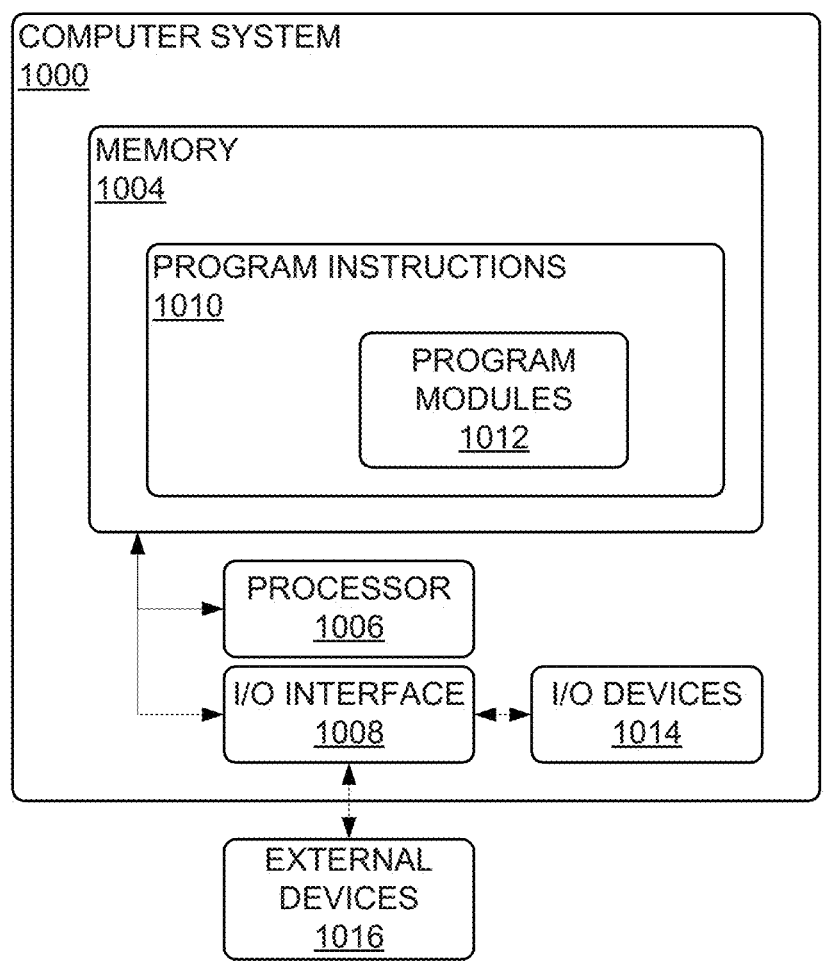
FIG. 10 is a diagram that illustrates an example computer system in accordance with one or more embodiments.

FIG. 10 is a diagram that illustrates an example computer/control system 1000 in accordance with one or more embodiments. In some embodiments, the system 1000 may be a programmable logic controller (PLC). The system 1000 may include a memory 1004, a processor 1006, and an input/output (I/O) interface 1008. The memory 1004 may include non-volatile memory (e.g., flash memory, read-only memory (ROM), programmable read-only memory (PROM), erasable programmable read-only memory (EPROM), electrically erasable programmable read-only memory (EEPROM)), volatile memory (e.g., random access memory (RAM), static random access memory (SRAM), synchronous dynamic RAM (SDRAM)), bulk storage memory (e.g., CD-ROM and/or DVD-ROM, hard drives), and/or the like. The memory 1004 may include a non-transitory computer-readable storage medium having program instructions 1010 stored therein. The program instructions 1010 may include program modules 1012 that are executable by a computer processor (e.g., the processor 1006) to cause the functional operations described herein, including drilling operations, logging operations, operations of the surface control unit 814, and/or the method 900.

The processor 1006 may be any suitable processor capable of executing/performing program instructions. The processor 1006 may include a central processing unit (CPU) that carries out program instructions (e.g., the program instructions of the program module(s) 1012) to perform the arithmetical, logical, and input/output operations described herein. The processor 2006 may include one or more processors. The I/O interface 1008 may provide an interface for communication with one or more I/O devices 1014, such as a joystick, a computer mouse, a keyboard, a display screen (e.g., an electronic display for displaying a graphical user interface (GUI)), and/or the like. The I/O devices 1014 may include one or more of the user input devices. The I/O devices 1014 may be connected to the I/O interface 1008 via a wired (e.g., Industrial Ethernet) or a wireless (e.g., Wi-Fi) connection. The I/O interface 1008 may provide an interface for communication with one or more external devices 1016, such as other computers, networks, and/or the like. In some embodiments, the I/O interface 1008 may include an antenna, a transceiver, and/or the like. In some embodiments, the computer system 1000 and/or the external devices 1016 may include one or more sensors, and/or the like.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described herein are to be taken as examples of embodiments. Elements and materials may be substituted for those illustrated and described herein, parts and processes may be reversed or omitted, and certain features of the embodiments may be utilized independently, all as would be apparent to one skilled in the art after having the benefit of this description of the embodiments. Changes may be made in the elements described herein without departing from the spirit and scope of the embodiments as described in the following claims. Headings used herein are for organizational purposes only and are not meant to be used to limit the scope of the description.

It will be appreciated that the processes and methods described herein are example embodiments of processes and methods that may be employed in accordance with the techniques described herein. The processes and methods may be modified to facilitate variations of their implementation and use. The order of the processes and methods and the operations provided therein may be changed, and various elements may be added, reordered, combined, omitted, modified, etc. Portions of the processes and methods may be implemented in software, hardware, or a combination thereof. Some or all of the portions of the processes and methods may be implemented by one or more of the processors/modules/applications described herein.

As used throughout this application, the word "may" is used in a permissive sense (i.e., meaning having the potential to), rather than the mandatory sense (i.e., meaning must). The words "include," "including," and "includes" mean including, but not limited to. As used throughout this application, the singular forms "a", "an," and "the" include plural referents unless the content clearly indicates otherwise. Thus, for example, reference to "an element" may include a combination of two or more elements. As used throughout this application, the phrase "based on" does not limit the associated operation to being solely based on a particular item. Thus, for example, processing "based on" data A may include processing based at least in part on data A and based at least in part on data B unless the content clearly indicates otherwise. As used throughout this application, the term "from" does not limit the associated operation to being directly from. Thus, for example, receiving an item "from" an entity may include receiving an item directly from the entity or indirectly from the entity (e.g., via an intermediary entity). Unless specifically stated otherwise, as apparent from the discussion, it is appreciated that throughout this specification discussions utilizing terms such as "processing," "computing," "calculating," "determining," or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical, electronic or magnetic quantities within memories, registers, or other information storage devices, transmission devices, or display devices of the special purpose computer or similar special purpose electronic processing/computing device.

What is claimed is:

1. A method for determining free water level (FWL) and rock type of a hydrocarbon reservoir, the method comprising:
    drilling, using a drilling system, a well comprising a wellbore extending into a formation of a hydrocarbon reservoir, the wellbore comprising a targeted reservoir section, and drilling the well comprising drilling the targeted reservoir section with steady overbalanced pressure to facilitate mud filtrate flushing;
    conducting, using a nuclear magnetic resonance (NMR) logging tool, a NMR logging operation of the targeted reservoir section to generate a nuclear magnetic resonance (NMR) log of the targeted reservoir section;
    conducting, using a resistivity logging tool, a resistivity logging of the targeted reservoir section to generate an uninvaded water saturation ($S_w$) log of the targeted reservoir section;
    determining, by a control unit, for each of a plurality of depths within the targeted reservoir section, a $T_2$ cutoff point for the depth that corresponds to a decay time at which a buoyancy pressure of hydrocarbon is about equal to reservoir capillary pressure at the depth, the $T_2$ cutoff for the depth determined based on a $T_2$ distribution of the NMR log for the depth, and a saturation ($S_w$) value of the uninvaded water saturation ($S_w$) log for the depth;
    identifying, by the control unit, a subset of the $T_2$ cutoff points across a subset depth interval in the targeted reservoir section that exhibit a hyperbolic trend;
    conducting, by the control unit, a curve fitting operation to determining a theoretical cutoff curve for the subset of the $T_2$ cutoff points, the curve fitting operation comprising a fitting based on a scaling factor (a) parameter and a depth parameter corresponding to a height above free water level (HAFWL);
    determining, by the control unit, a FWL of the reservoir based on, for at least one point on the theoretical cutoff curve, a true vertical depth for the point and an HAFWL for the point on the theoretical cutoff curve; and
    determining, by the control unit, a rock type of the reservoir corresponding to the scaling factor (a).

2. The method of claim 1, wherein drilling the well comprises adding surfactant to a water based mud (WBM) used in the drilling process to facilitate reduced interfacial tension to maximize sweep in a flushed zone of the wellbore.

3. The method of claim 1, wherein conducting the NMR logging operation of the targeted reservoir section to generate the NMR log of the targeted reservoir section comprises minimizing an echo spacing (TE) of the NMR logging operation, and employing a relatively large number of echoes.

4. The method of claim 1, wherein conducting the resistivity logging of the targeted reservoir section to generate the uninvaded water saturation ($S_w$) log of the targeted reservoir section comprises acquiring triple combo logs and performing uninvaded reservoir water saturation analysis of the triple combo logs.

5. A method for determining characteristics of a hydrocarbon reservoir, the method comprising:
    conducting, using a nuclear magnetic resonance (NMR) logging tool, a nuclear magnetic resonance (NMR) logging operation of a targeted reservoir section of a wellbore extending into a hydrocarbon reservoir to generate a nuclear magnetic resonance (NMR) log of the targeted reservoir section;
    conducting, using a resistivity logging tool, a resistivity logging of the targeted reservoir section to generate an uninvaded water saturation ($S_w$) log of the targeted reservoir section;
    determining, by a control unit, for each of a plurality of depths in the targeted reservoir section, a $T_2$ cutoff point for the depth based on values of the NMR log and the uninvaded water saturation ($S_w$) log for the depth;
    identifying, by the control unit, a subset of the T2 cutoff points that exhibit a hyperbolic trend;

determining, by the control unit, a theoretical cutoff curve corresponding to the subset of the T2 cutoff points;

determining, by the control unit, a free water level (FWL) of the reservoir based on the theoretical cutoff curve; and determining, by the control unit, a rock type of the reservoir based on the theoretical cutoff curve.

6. The method of claim 5, further comprising drilling the wellbore, wherein the drilling of the wellbore comprises drilling the targeted reservoir section with steady overbalanced pressure to facilitate reduced interfacial tension to maximize sweep in a flushed zone of the wellbore.

7. The method of claim 5, further comprising drilling the wellbore, wherein the drilling of the wellbore comprises adding surfactant to a water based mud (WBM) used in the drilling process to facilitate reduced interfacial tension to maximize sweep in a flushed zone of the wellbore.

8. The method of claim 5, wherein conducting the NMR logging operation of the targeted reservoir section to generate the NMR log of the targeted reservoir section comprises minimizing an echo spacing (TE) of the NMR logging operation.

9. The method of claim 5, wherein conducting the NMR logging operation of the targeted reservoir section to generate the NMR log of the targeted reservoir section comprises employing a relatively large number of echoes.

10. The method of claim 5, wherein conducting the resistivity logging of the targeted reservoir section to generate the uninvaded water saturation ($S_w$) log of the targeted reservoir section comprises acquiring triple combo logs and performing uninvaded reservoir water saturation analysis of the triple combo logs.

11. The method of claim 5, wherein the $T_2$ cutoff point for each depth corresponds to a time at which a buoyancy pressure of hydrocarbon is about equal to pore capillary pressure at the depth, the $T_2$ cutoff determined based on a $T_2$ distribution of the NMR log for the depth, and a saturation ($S_w$) value of the uninvaded water saturation ($S_w$) log for the depth.

12. The method of claim 5, wherein determining a theoretical cutoff curve corresponding to the subset of the $T_2$ cutoff points comprises using a curve fitting operation considering a fit to the subset of the $T_2$ cutoff points based on a scaling factor (a) parameter and a depth parameter corresponding to a height above free water level (HAFWL).

13. The method of claim 12, wherein determining a FWL of the reservoir based on the theoretical cutoff curve comprises determining, for at least one point on the theoretical cutoff curve, a true vertical depth for the point and an HAFWL for the point on the theoretical cutoff curve, and wherein the FWL is a summation of the true vertical depth for the point and the HAFWL for the point.

14. The method of claim 12, wherein determining a rock type of the reservoir based on the theoretical cutoff curve comprises determining a rock type of the reservoir corresponding to the scaling factor (a).

15. A system for determining characteristics of a hydrocarbon reservoir, the system comprising:

a logging system comprising:
    a nuclear magnetic resonance (NMR) logging system configured conduct a nuclear magnetic resonance (NMR) logging operation of a targeted reservoir section of a wellbore extending into a hydrocarbon reservoir to generate a nuclear magnetic resonance (NMR) log of the targeted reservoir section; and
    a resistivity logging system configured to conduct a resistivity logging of the targeted reservoir section to generate an uninvaded water saturation ($S_w$) log of the targeted reservoir section; and a control unit configured to:
    determine, for each of a plurality of depths in the targeted reservoir section, a $T_2$ cutoff point for the depth based on values of the NMR log and the uninvaded water saturation ($S_w$) log for the depth;
    identify a subset of the $T_2$ cutoff points that exhibit a hyperbolic trend;
    determine a theoretical cutoff curve corresponding to the subset of the $T_2$ cutoff points;
    determine a free water level (FWL) of the reservoir based on the theoretical cutoff curve; and
    determine a rock type of the reservoir based on the theoretical cutoff curve.

16. The system of claim 15, further comprising a drilling system configured to drill the wellbore, wherein the drilling of the wellbore comprises drilling the targeted reservoir section with steady overbalanced pressure to facilitate reduced interfacial tension to maximize sweep in a flushed zone of the wellbore.

17. The system of claim 15, further comprising a drilling system configured to drill the wellbore, wherein the drilling of the wellbore comprises adding surfactant to a water based mud (WBM) used in the drilling process to facilitate reduced interfacial tension to maximize sweep in a flushed zone of the wellbore.

18. The system of claim 15, wherein conducting the NMR logging operation of the targeted reservoir section to generate the NMR log of the targeted reservoir section comprises minimizing an echo spacing (TE) of the NMR logging operation.

19. The system of claim 15, wherein conducting the NMR logging operation of the targeted reservoir section to generate the NMR log of the targeted reservoir section comprises employing a relatively large number of echoes.

20. The system of claim 15, wherein conducting the resistivity logging of the targeted reservoir section to generate the uninvaded water saturation ($S_w$) log of the targeted reservoir section comprises acquiring triple combo logs and performing uninvaded reservoir water saturation analysis of the triple combo logs.

21. The system of claim 15, wherein the $T_2$ cutoff point for each depth corresponds to a time at which a buoyancy pressure of hydrocarbon is about equal to pore capillary pressure at the depth, the $T_2$ cutoff determined based on a $T_2$ distribution of the NMR log for the depth, and a saturation ($S_w$) value of the uninvaded water saturation ($S_w$) log for the depth.

22. The system of claim 15, wherein determining a theoretical cutoff curve corresponding to the subset of the $T_2$ cutoff points comprises using a curve fitting operation considering a fit to the subset of the $T_2$ cutoff points based on a scaling factor (a) parameter and a depth parameter corresponding to a height above free water level (HAFWL).

23. The system of claim 22, wherein determining a FWL of the reservoir based on the theoretical cutoff curve comprises determining, for at least one point on the theoretical cutoff curve, a true vertical depth for the point and an HAFWL for the point on the theoretical cutoff curve, and wherein the FWL is a summation of the true vertical depth for the point and the HAFWL for the point.

24. The system of claim 22, wherein determining a rock type of the reservoir based on the theoretical cutoff curve comprises determining a rock type of the reservoir corresponding to the scaling factor (a).

25. A non-transitory computer readable medium comprising program instructions stored thereon for determining characteristics of a hydrocarbon reservoir, the program instructions executable by one or more computer processors to perform the following:

conducting, using a nuclear magnetic resonance (NMR) logging tool, a nuclear magnetic resonance (NMR) logging operation of a targeted reservoir section of a wellbore extending into a hydrocarbon reservoir to generate a nuclear magnetic resonance (NMR) log of the targeted reservoir section;

conducting, using a resistivity logging tool, a resistivity logging of the targeted reservoir section to generate an uninvaded water saturation ($S_w$) log of the targeted reservoir section;

determining, by a control unit, for each of a plurality of depths in the targeted reservoir section, a $T_2$ cutoff point for the depth based on values of the NMR log and the uninvaded water saturation ($S_w$) log for the depth;

identifying, by the control unit, a subset of the $T_2$ cutoff points that exhibit a hyperbolic trend;

determining, by the control unit, a theoretical cutoff curve corresponding to the subset of the $T_2$ cutoff points;

determining, by the control unit, a free water level (FWL) of the reservoir based on the theoretical cutoff curve; and determining, by the control unit, a rock type of the reservoir based on the theoretical cutoff curve.

\* \* \* \* \*